US008071371B2

(12) United States Patent
Lanzavecchia (10) Patent No.: US 8,071,371 B2
(45) Date of Patent: Dec. 6, 2011

(54) MONOCLONAL ANTIBODY PRODUCTION BY EBV TRANSFORMATION OF B CELLS

(75) Inventor: Antonio Lanzavecchia, Bellinzona (CH)

(73) Assignee: Humabs LLC, San Francisco, CA (US)

( * ) Notice: Subject to any disclaimer, the term of this patent is extended or adjusted under 35 U.S.C. 154(b) by 1133 days.

(21) Appl. No.: 11/719,835

(22) PCT Filed: Feb. 26, 2004

(86) PCT No.: PCT/IB2004/001071
§ 371 (c)(1),
(2), (4) Date: May 21, 2007

(87) PCT Pub. No.: WO2004/076677
PCT Pub. Date: Sep. 10, 2004

(65) Prior Publication Data
US 2010/0021470 A1 Jan. 28, 2010

Related U.S. Application Data

(60) Provisional application No. 60/516,665, filed on Oct. 30, 2003.

(30) Foreign Application Priority Data

| Feb. 26, 2003 | (GB) | 0304363.5 |
| Aug. 6, 2003 | (GB) | 0318431.4 |
| Oct. 30, 2003 | (GB) | 0325391.1 |

(51) Int. Cl.
C12N 5/06 (2006.01)
C12N 5/00 (2006.01)
C12N 5/02 (2006.01)

(52) U.S. Cl. .......... 435/326; 435/346; 435/375

(58) Field of Classification Search .......... None
See application file for complete search history.

(56) References Cited

U.S. PATENT DOCUMENTS

| 4,464,465 A | 8/1984 | Lostrom |
| 4,997,764 A | 3/1991 | Favera |
| 5,106,738 A | 4/1992 | Hanna, Jr. |
| 7,223,741 B2 | 5/2007 | Krieg |
| 7,868,139 B2 * | 1/2011 | Elson et al. .......... 530/350 |
| 2003/0026782 A1 | 2/2003 | Krieg |
| 2003/0191079 A1 | 10/2003 | Krieg |
| 2004/0087534 A1 | 5/2004 | Krieg |
| 2004/0087538 A1 | 5/2004 | Krieg |
| 2004/0106568 A1 | 6/2004 | Krieg |
| 2004/0142469 A1 | 7/2004 | Krieg |
| 2004/0143112 A1 | 7/2004 | Krieg |
| 2004/0152656 A1 | 8/2004 | Krieg |
| 2004/0152657 A1 | 8/2004 | Krieg |
| 2004/0162258 A1 | 8/2004 | Krieg |
| 2004/0162262 A1 | 8/2004 | Krieg |
| 2004/0171150 A1 | 9/2004 | Krieg |
| 2004/0181045 A1 | 9/2004 | Krieg |
| 2005/0059625 A1 | 3/2005 | Krieg |

FOREIGN PATENT DOCUMENTS

| EP | 0505397 B1 | 9/1992 |
| WO | 8900607 | 1/1989 |
| WO | 9006994 | 6/1990 |
| WO | 9424164 | 10/1994 |
| WO | 9514780 | 6/1995 |
| WO | 9602555 | 2/1996 |
| WO | 9818810 | 5/1998 |
| WO | 2007068758 | 6/2007 |

OTHER PUBLICATIONS

Banchereau, J. et al; Growing human B lymphocytes in the CD40 system, Nature 353: 678-679, (1991).
Tsuchiyama et al; "Synergy between anti-CD40 MAb and Epstein-Barr virus in activation and transformation of human B lymphocytes.","Human Antibodies 8: 43-47", (1997).
Madec, A.M., et al; Four IgG anti-islet human monoclonal antibodies isolated from a type 1 diabetes patient recognize distinct epitopes of glutamic acid decarboxylase 65 and are somatically mutated, Journal of Immunology 156:3541-9, (1996).
Peyron, E. et al; Human monoclonal autoantibodies specific for the *Bullous pemphigoid* antigen 1 (BPAg 1). Journal of Immunology 153: 1333-1339 (1994).
Visco, V. et al; Human IgG monoclonal antibodies that modulate the binding of specific IgE to birch pollen Bet v 1., Journal of Immunology 157:956-62. (1996).
Bernasconi, et al; Maintenance of Serological Memory by Polyclonal Activation of Human Memory B Cells, Science 298: 2199-2202 (2002).
Jung, et al; Distinct Response of Human B Cell Subpopulations in Recognition of an Innate Immune Signal, CpG DNA, J. Immunol. 169: 2368-2373 (2002).
Tangye, et al; A Division-Linked mechanism for the Rapid Generation of Ig-Secreting Cells From Human Memory B Cells, J. Immunol. 170: 261-269 (2003).
Tangye, et; Intrinsic Differences in the Proliferation of Naive and Memory Human B Cells as a Mechanism of Enhanced Secondary Immune, J. Immunol. 170: 686-694 (2003).
Baba, et al; Human Neutralizing Monoclonal Antibodies of the igG1 Subtype Protect Against Mucosal Simian-Human Immunodeficiency Virus Infection, Nature Medicine 6: 200-206 (2000).
Niedbala et al; A Comparison of Three Methods for Production of Human Hybridomas Secreting Autoantibodies, Hybridoma 17: 299-304 (1998).
Mulder et al; A Human Monoclonal Antibody, Produced Following In Vitro Immunization, Recognizing An Epitope Shared by HLA-A2 Subtypes and HLA-A28 Tissue Antigens, Tissue Antigens, 42: 27-34 (1993).

(Continued)

*Primary Examiner* — Michail Belyavskyi
(74) *Attorney, Agent, or Firm* — Dennis A. Bennett; Suman R. Mirmira (57) ABSTRACT

A method for producing a clone of an immortalized human B memory lymphocyte, comprising the step of transforming human B memory lymphocytes using Epstein Barr Virus (EBV) in the presence of a polyclonal B cell activator. The method is particularly useful in a method for producing a clone of an immortalized human B memory lymphocyte capable of producing a human monoclonal antibody with a desired antigen specificity, comprising the steps of: (i) selecting and isolating a human memory B lymphocyte subpopulation; (ii) transforming the subpopulation with Epstein Barr Virus (EBV) in the presence of a polyclonal B cell activator; (iii) screening the culture supernatant for antigen specificity; and (iv) isolating an immortalized human B memory lymphocyte clone capable of producing a human monoclonal antibody having the desired antigen specificity.

30 Claims, 4 Drawing Sheets

OTHER PUBLICATIONS

Drosten et al; Identification of a novel Coronavirus in Patients with Severe Acute Respiratory Syndrome, New England Journal of Medicine, 348: 1967-1976 (2003).
Takeda et al. (2003). Toll-like receptors. Annu Rev Immunol 21, 335-376.
Bron et al. (1984). "Production of human monoclonal IgG antibodies against Rhesus (D) antigen." Proc Natl Acad Sci U S A 81(10): 3214-7.
Casali et al. (1986). "Human monoclonals from antigen-specific selection of B lymphocytes and transformation by EBV." Science 234(4775): 476-9.
Diebold et al. (2004). Innate Antiviral Responses by Means of TLR7-Mediated Recognition of Single-Stranded RNA. Science. Feb. 19, 2004 [Epub ahead of print].
Thompson et al. (1986). "The efficient production of stable, human monoclonal antibody-secreting hybridomas from EBV-transformed lymphocytes using the mouse myeloma X63-Ag8.653 as a fusion partner." J Immunol Methods 94 (1-2): 7-12.
Giachino et al. (1995) "kappa+lambda+ dual receptor B cells are present in the human peripheral repertoire." J Exp Med 181, 1245-50.
Hartmann et al. (2000). "Delineation of a CpG phosphorothioate oligodeoxynucleotide for activating primate immune responses in vitro and in vivo." J Immunol 164(3): 1617-24.
Heil et al. (2004). Species-Specific Recognition of Single-Stranded RNA via Toll-like Receptor 7 and 8. Science. Feb. 19, 2004 [Epub ahead of print].
Steinitz et al. (1984). "Human anti-pneumococci antibody produced by an Epstein Barr virus (EBV)-immortalized cell line." J Immunol 132(2): 877-82.
Ifversen et al. (1993). "Effect of cell-derived growth factors and cytokines on the clonal outgrowth of EBV-infected B cells and established lymphoblastoid cell lines." Hum Antibodies Hybridomas 4(3): 115-23.
Johanson et al. (1997). "Development of a humanized monoclonal antibody (MEDI-493) with potent in vitro and in vivo activity against respiratory syncythial virus." J Infect Dis 176: 1215-24.
Karber (1931). "50% end-point calculation". Arch. Exp. Pathol. Pharmak. 162, 480-483.
Kohler & Milstein (1975). "Continuous cultures of fused cells secreting antibody of predefined specificity." Nature 256 (5517): 495-7.
Kozbor & Roder (1981). "Requirements for the establishment of high-titered human monoclonal antibodies against tetanus toxoid using the Epstein-Barr virus technique." J Immunol 127(4): 1275-80.
Kozbor et al. (1982). "Human anti-tetanus toxoid monoclonal antibody secreted by EBV-transformed human B cells fused with murine myeloma." Hybridoma 1(3): 323-8.
Krieg (2002). "CpG motifs in bacterial DNA and their immune effects." Annu Rev Immunol 20: 709-60.
Krieg et al. (1995). "CpG motifs in bacterial DNA trigger direct B-cell activation." Nature 374(6522): 546-9.
Ksiazek et al. (2003). "A novel coronavirus associated with severe acute respiratory syndrome" N Engl J Med 348 (20):1953-66.
Lanzavecchia (1985). "Antigen-specific interaction between T and B cells." Nature 314(6011): 537-9.
Lundgren et al. (1983). "Monoclonal anti-parasite and anti-RBC antibodies produced by stable EBV-transformed B cell lines from malaria patients." J Immunol 131(4): 2000-3.
Medzhitov & Janeway (2000). "Innate immune recognition: mechanisms and pathways." Immunol Rev 173:89 97.
Medzhitov & Janeway (2002). "Decoding the patterns of self and nonself by the innate immune system" Science 296:298-300.
Rosen et al. "Polyclonal Ig production after Epstein-Barr virus infection of human lymphocytes in vitro." Nature 267 (5607): 52-4.
Rosen et al. (1983). "Human monoclonal antibodies to a genus-specific chlamydial antigen, produced by EBV-transformed B cells." J Immunol 130(6): 2899-902.
Schneider et al. (1999) "BAFF, a novel ligand of the tumor necrosis factor family, stimulates B cell growth". J Exp Med 189(11):1747-56.
Steinitz et al. (1980). "Continuous production of monoclonal rheumatoid factor by EBV-transformed lymphocytes." Nature 287(5781): 443-5.
Steinitz et al. (1977). "EB virus-induced B lymphocyte cell lines producing specific antibody." Nature 269(5627): 420-2.
Hornung, Veit et al, Replication-Dependent Potetn IFN-alpha Induction in Human Plasmacytoid Dendritic Cells by a Single-Stranded RNA Virus, Journal of Immunology, 2004, 5935-5943.
Guo, Yong-Mei, et al, CpG-ODN 2006 and Human Parvovirus B19 Genome Consensus Sequences Selectively Inhibit Growth and Development of Erythroid Progenitor Cells, Blood, 2010, 115, 4569-4579.
Hartmann, Mechanism and Function of a Newly Identified CpG DNA Motif in Human Primary B Cells, J Immunol 2000; 165; 944-953.
Fraussen, A Novel Method for making human monoclonal antibodies, Journal of Autoimmunity, 2010, 35, 130-134.
Hemmi, Hiroaki, et al, Small Anti-Viral Compounds Acitvate Immune Cells Via the TLR7 MyD88-dependent signaling pathway, Nature Immunology, vol. 3, No. 2, Feb. 2002, 196-200.
Schlaepfer, Erika et al, TLR7/8 Triggering Exerts Opposing Effects in Acute Versus Latent HIV Infection, J Immunol 2006; 176; 2888-2895.
Vollmer, Jorg, Immunopharmacology of CpG Oligodeoxynucleotides and Ribavirin, Antimicrobial Agents and Chemotherapy, 2004, 2314-2317, vol. 48, No. 6.
Bernasconi, Nadia L., A role for Toll-like receptors in Acquired immunity: up-regulation of TLR9 by BCR triggering in naive B cells and constitutive Expression in Memory B Cells, 2003, 101, 4500-4504.
Blazar, Bruce, et al, Synthetic Unmethylated Cytosine-phosphate-guanosine oligodeoxynucleotides are potent stimulators of antileukemia responses in naive and bone marrow transplant recipients, Blood, 2001, 98; 1217-1225.
InVivoGen, ODN 2006, Cat No. tlrl-2006.
Australian Exam Report for application No. 2004215125 (Corresponding AU Case). Date Mailed: Apr. 14, 2009.
Communication from Australian Patent Office, Notice of Acceptance, Application No. 2004215125 (Corresponding AU Case), Mailed Dec. 21, 2010.
Communication from EPO in Corresponding EP Case re Third Party Observations. Application No. 04714866.3-2401. Mailed Aug. 18, 2008.
Communication from the European Patent Office, Application No. 04714866.3-2401 (Corresponding EP Case). Mailed Aug. 25, 2008.
Communication from the European Patent Office, Application No. 04714866.3-2401 (Corresponding EP Case). Mailed Sep. 18, 2009.
Communication from the European Patent Office, Application No. 04714866.3-2401 (Corresponding EP Case). Mailed Jan. 4, 2011.
Communication from EPO in Corresponding EP Case re Third Party Observations filed with EPO. Application No. 04714866.3-2401, Date Mailed Apr. 11, 2011.
Communication from the Singaporean Patent Office, Invitation to Respond to Written Opinion, Application No. 200717186-1 (Corresponding SG Case), Mailed Aug. 25, 2009.
Communication from the Singaporean Patent Office, Invitation to Respond to Written Opinion, Application No. 200717186-1 (Corresponding SG Case), Mailed Sep. 23, 2010.
Communication from the Australian Patent Office: Notice of Acceptance of Application No. 2011201553 (Divisional of Corresponding AU Application). Mailed May 23, 2011.
Communication from the Singaporean Intellectual Property Office: Invitation to Respond to Written Opinion, Application No. 200717186-1 (Corresponding SG Case). Mailed Jun. 10, 2011.
Communication to the European Patent Office from Third Party re Application No. 04714866.3-2401 (Corresponding EP Case). Filed with EPO on Jun. 10, 2011.
Communication from the European Patent Office re Communication from Third Party re Application No. 04714866.3-2401 (Corresponding EP Case). Mailed Jun. 17, 2011.
Communication Pursuant to Article 94(3) EPC from the European Patent Office re Application No. 04714866.3 (Corresponding EP Case). Mailed Jul. 13, 2011.
US 6,008,200, 12/1999, Krieg (withdrawn)

* cited by examiner

MONOCLONAL ANTIBODY PRODUCTION BY EBV TRANSFORMATION OF B CELLS

All documents cited herein are incorporated by reference in their entirety.

TECHNICAL FIELD

This invention relates to monoclonal antibodies, to a method for preparing immortalised memory B cells, to a method for preparing immortalised memory B cells capable of producing a monoclonal antibody with a desired antigen specificity and to the use of antibodies produced by said immortalised memory B cells. The invention is particularly useful for preparing human monoclonal antibodies. In one embodiment, the invention relates to a method for preparing immortalised human memory B cells capable of producing antibodies specific for an infectious agent, more particularly where the infectious agent is the severe acute respiratory syndrome (SARS) virus. Further embodiments are described below.

BACKGROUND ART

The success in generating murine monoclonal antibodies rests on the efficient and selective fusion of antigen-stimulated B cell blasts with a murine myeloma cell line followed by selection of stable antibody producing hybrids (Kohler & Milstein 1975). FR2817875 describes a modified version of this protocol where prior to immortalisation, B lymphocytes are induced to differentiate by a non-specific activating system and a cytokine. The B cell blasts may be taken from the spleen or lymph nodes. However, the difficulty in obtaining antigen-stimulated B cell blasts and the lack of suitable fusion partners has hampered this approach in the human system.

As an alternative approach to making human antibodies, Epstein Barr Virus (BV) has been used to immortalize human (and primate) B cells producing specific antibodies. The EBV method has been described in several publications since 1977 (Rosen et al. 1977; Steinitz et al. 1977; Steinitz et al. 1980; Kozbor & Roder 1981; Lundgren et al. 1983; Rosen et al. 1983; Steinitz et al. 1984; Lanzavecchia 1985). B cells are immortalized by infection with EBV and growing clones secreting specific antibodies are selected. The method does not require antigenic boost, since EBV immortalizes also resting human B cells. However, the EBV-based method has several limitations, namely the low efficiency of immortalization, the low cloning efficiency of EBV-immortalized B cells, the slow grown rate and, in some cases, low antibody production. U.S. Pat. No. 5,499,7764 describes a method of improving the growth rate of the EBV immortalised cells comprising transfecting EBV infected B cells with activated c-myc DNA. This confers on the cells the ability to grow in semi-solid media and to grow in hosts such as rats and mice. WO95/13089 describes the use of GM-CSF and IL-3 to stimulate the release of antibody by B cells. Boimkanim et al. (U.S. Pat. No. 5,798,230) have overcome the problem of low production of antibodies by inactivating EBNA2. However, this does not solve the problem of low efficiency of immortalization. To circumvent these problems some authors carried out an enrichment for antigen-specific B cells before EBV immortalization using for instance biotinylated soluble antigens (Casali et al. 1986). Others proposed the fusion of the EBV-immortalised cells with mouse myelomas or human-mouse heteromyelomas to exploit the higher growth rate and Ig secretion of the hybrids (Kozbor et al. 1982; Bron et al 1984; Thompson et al. 1986). Claims that the cloning efficiency could be increased by cell-derived growth factors such as thioredoxin have been made in a publication (Ifversen et al. 1993), but these results have neither been confirmed nor utilized, even by the same authors. In conclusion, although the EBV method has in principle some advantages, it has been abandoned because of the low efficiency of immortalization and cloning.

Another reason why the EBV method has become obsolete is that alternative approaches for making human or human-like monoclonal antibodies became available through genetic engineering. These include the humanization of murine antibodies, the isolation of antibodies from libraries of different complexity and the production of hybridomas using the classical method in mice transgenic for human Ig loci (the "xenomouse"). The literature on these alternative approaches is not reviewed here since is not directly relevant to the present invention. However, it is worth considering some limitations of these methods. Humanization of murine monoclonal antibodies is a laborious and incomplete procedure. Random antibody libraries represent an unbiased repertoire and can therefore be used to select antibody specificities against highly conserved antigens, but lead to antibodies of low affinity. Libraries selected from antigen primed B cells are enriched for a particular specificity, but do not preserve the original VH-VL pairing and generally lead to antibodies that have lower affinity for the antigen than those present in the original antibody repertoire. The impact of this technology has been limited. In contrast the xeno-mouse can be efficiently immunized against an antigen of choice (especially if this is a human antigen), but this system shares with the classical murine hybridoma technology the limitation that the antibodies are selected in a species other than human. Therefore these methods are not suitable to produce antibodies with the characteristics of those produced in the course of a physiological human immune response. This applies to the antibody response to human pathogens including HIV, the four *Plasmodium* species that cause malaria in humans (*P. falciparum, P. vivax, P. malariae* and *P. ovale*), human hepatitis B and C viruses, Measles virus, Ebola virus etc. (for an exhaustive list see Fields et al. 1996). It also applies to antibody responses to environmental allergens generated in allergic patients, to tumour antigens generated in tumour bearing patients and to self antigens in patients with autoimmune diseases.

There is therefore a need for an efficient method of production of human monoclonal antibodies that have been selected in the course of the natural immune response.

DISCLOSURE OF THE INVENTION

While the present invention is illustrated by embodiments where human monoclonal antibodies are produced, the techniques described herein are not so limited. The present invention can be used for any species for which it is desired to produce monoclonal antibodies efficiently.

The invention is based on the discovery that a polyclonal B cell activator (such as CpG sequences) enhances the efficiency of EBV immortalization and of cloning EBV-immortalized cells. This increased efficiency represents a quantum leap that makes the EBV technique suitable for the rapid isolation of large numbers of human monoclonal antibodies from the memory repertoire with no need for specific immunization or boosting. Antibodies are selected from the physiological immunocompetent environment stimulated by natural contact with a pathogen or antigen. The method is therefore particularly useful to produce antibodies against antigenic determinants that are specifically recognised by the human immune system. These include neutralizing antibodies to human pathogens and antibodies to allergens, tumour antigens, auto-antigens and allo-antigens that are part of the memory repertoire of a given individual. There is therefore no need for disease models to be created or for immunization with purified antigens. The antibodies of the current invention are also fully human (including native post-translational modifications when expressed in B cells) and exploit all the diversity generated in the course of a human immune response (affinity maturation).

Thus, the invention provides inter alia a method for producing immortalised human B memory lymphocytes, comprising the step of transforming human B memory lymphocytes using Epstein Barr virus (EBV) in the presence of a polyclonal B cell activator. The method permits extremely high efficiency transformation for the first time.

In a further aspect, the invention provides a method for producing a clone of an immortalised human B memory lymphocyte capable of producing a human monoclonal antibody with a desired antigen specificity, comprising the steps of:
  (i) transforming a population of cells comprising or consisting of human memory B lymphocytes with Epstein Barr Virus (EBV) in the presence of a polyclonal B cell activator;
  (ii) screening the culture supernatant for antigen specificity; and
  (iii) isolating an immortalised human B memory lymphocyte clone capable of producing a human monoclonal antibody having the desired antigen specificity.

The methods of the invention have already been used to clone human memory B lymphocyte with up to 100% efficiency. EBV-transformed B cell clones that produce neutralizing IgG antibodies specific for measles virus, the *Plasmodium* species that cause malaria in humans, tetanus toxoid, *Toxoplasma gondii* and alloantigens have been produced using this procedure. Furthermore, EBV-transformed B cell clones that produce neutralizing IgG antibodies specific for the SARS coronavirus (CoV) have also been produced. It will be appreciated that the method can be transferred and used for the production of antibodies against any specificity that is present in the human memory repertoire.

The sudden emergence of SARS in 2002 in China caused hundreds of deaths in a number of countries. The causative agent was unknown and as such there was no cure available. It has since been discovered that the syndrome is caused by a new type of coronavirus (Drosten et al. 2003; Ksiazek et al. 2003) and methods to detect this virus and combat infections caused by it are required.

In a preferred aspect, the invention provides a method for producing a clone of immortalised human B memory lymphocytes capable of producing a human monoclonal antibody specific for the SARS virus, comprising the steps of:
  (i) transforming a population of cells comprising or consisting of human memory B lymphocytes with Epstein Barr Virus (EBV) in the presence of a polyclonal B cell activator,
  (ii) screening the culture supernatant for specificity for the SARS virus, and
  (iii) isolating an immortalised human B memory lymphocyte clone capable of producing a human monoclonal antibody having specificity for the SARS virus.

In this specification, the term "antibody having specificity for the SARS virus" means that an antibody molecule binds to the coronavirus that is the causative agent of SARS with a greater affinity compared to its binding affinity for other viruses.

Generally, the invention also provides a method for producing immortalised human B memory lymphocytes, comprising a step of transforming a population of human B memory lymphocytes, wherein the method transforms $\geq$n % of the human B memory lymphocytes in the population. The value of n is selected from 2, 3, 4, 5, 10, 20, 30, 40, 50, 60, 70, 80, 90 and 100. After the immortalised cells are produced then they can be screened to select cells that produce antibodies with a desired specificity. Selected cells can then be used for monoclonal antibody production. This method preferably does not involve cellular fusion of the B memory lymphocytes with other cells.

Polyclonal Activators

In this specification, the term "polyclonal activator" means a molecule or compound or a combination thereof that activates B lymphocytes irrespective of their antigenic specificity. A range of different molecules may be used as the polyclonal activator.

Toll Like Receptors (TLRs) are pattern recognition receptors of the innate immune system expressed on a variety of cells including dendritic cells and B cells (Medzhitov & Janeway 2000, 2002). TLR agonists include microbial products and synthetic compounds. Preferred polyclonal activators are agonists of the Toll Like Receptors which are expressed on memory B cells, such as TLR-7, TLR-9 and TLR-10 (Bernasconi et al. 2003). Such molecules may be of microbial or cellular origin or synthetic.

Unmethylated DNA oligonucleotides (CpG) are TLR-9 agonists. They stimulate dendritic cell maturation and activate B cell proliferation and differentiation polyclonally, i.e. irrespective of the antibody specificity (Krieg et al. 1995; Krieg 2002). The biological effect of CpG is dependent on specific sequences and chemical modifications (Krieg 2002). CpG oligonucleotides can be used as polyclonal activators, and examples of suitable activators are CpGs such as CpG 2006 (5'-TCGTCGTTTTGTCGTTTTGTCGTT-3' (SEQ ID NO: 1); Hartmann et al. 2000) and other oligonucleotide sequences that trigger TLR-9. By "CpG" we mean sequences of unmethylated DNA oligonucleotides. More particularly, the term "CpG" includes single-stranded DNA molecules of between 5 and 100 nucleotides in length (e.g. 10-80, 20-70, 30-60 nucleotides) that include one or more instances (e.g. 2, 4, 6, 8, 10 or more) of the dinucleotide CG sequence, with the C in the dinucleotide(s) being unmethylated.

Imidazoquinoline compounds, such as R-848 (resiquimod), trigger TLR-7 and TLR-8 and stimulate dendritic cell maturation (Hemmi et al. 2002). Such compounds can be used as polyclonal activators with the invention e.g. R-848 (and its analogs) and other synthetic compounds that trigger TLR-7 and TLR-8, including but not limited to: imiquimod, loxoribine, and guanosine analogs (e.g. 7-thia-8-oxoguanosine and 7-deazaguanosine).

Other polyclonal activators include other agonists of TLRs and of other pattern recognition receptors (PRRs) that are expressed on B memory cells, including monoclonal antibodies specific for TLRs. Additional polyclonal activators include CD40L, BAFF (B-cell activating factor, Schneider et al. 1999, also known as tumor necrosis factor superfamily member 13B, BLyS, or THANK), antibodies specific for CD40 and other molecules expressed by dendritic cells and activated T cells. In these cases the cells themselves may be used as polyclonal activators.

Polyclonal activators may also include PAMPs pathogen-associated molecular patterns), such as lipopolysaccharide (LPS), peptidoglycans, flagellins, zymosans and other cell wall components found in pathogens. Other available polyclonal activators include loxoribine, heat-killed *Achole-*

*plasma ladiawii*, heat-killed *Listeria monocytogenes*, lipoteichoic acids, tripalmitoylated lipopeptides (e.g. $Pam_3CSK4$), single-stranded RNA (Diebold et al. 2004; Heil et al. 2004), double-stranded RNA, poly(I:C), bacterial DNAs, etc. A detailed list of TLR agonists can be found in Takeda et al. (2003). Some activators are not preferred for use with human B cells e.g. LPS.

In a particularly preferred aspect, CpG 2006 is used as the polyclonal activator.

Commercial suppliers of suitable polyclonal activators include Invivogen.

Recently it has been shown that human memory B cells are selectively stimulated by CpG (Bernasconi et al. 2002), and that several TLRs are selectively expressed on human memory B cells but not on naïve B cells (Bernasconi et al. 2003, the entire contents of which are herein incorporated by reference).

Transforming B Cells

In methods of the invention, cells can be transformed with EBV in the presence of a polygonal B cell activator. Transformation with EBV is a standard technique and can easily be adapted to include polyclonal B cell activators.

Additional stimulants of cellular growth and differentiation may be added during the transformation step to further enhance the efficiency. These stimulants may be cytokines such as IL-2 and IL-15. In a particularly preferred aspect, IL-2 is added during the immortalisation step to further improve the efficiency of immortalisation, but its use is not essential.

The memory B cells to be transformed can come from various sources (e.g. from whole blood, from peripheral blood mononuclear cells (PBMCs), from blood culture, from bone marrow, from organs, etc.), and suitable methods for obtaining human B cells are well known in the art. Samples may include cells that are not memory B cells e.g. other blood cells. A specific human memory B lymphocyte subpopulation exhibiting a desired antigen specificity may be selected before the transformation step by using methods known in the art. In one embodiment, the human memory B lymphocyte subpopulation has specificity for the SARS virus e.g. the B cells are taken from a patient who is suffering or has recovered from SARS. In another embodiment, B cells are taken from subjects with Alzheimer's disease and include B cells with specificity for β-amyloid (e.g. Hock et al. (2002) *Nature Medicine* 8:1270-75; Mattson & Chan (2003) *Science* 301:1847-9; etc.).

As an alternative to using EBV, other equivalent lymphocyte transforming agents may be used, including other viruses that can transform B cells. EBV is suitable for transforming the B cells of most primates but, for other organisms, suitable viruses can be selected.

Screening and Isolation of B Cells

Transformed B cells are screened for those having the desired antigen specificity, and individual B cell clones can then be produced from the positive cells.

The screening step may be carried out by ELISA, by staining of tissues or cells (including transfected cells), a neutralisation assay or one of a number of other methods known in the art for identifying desired antigen specificity. The assay may select on the basis of simple antigen recognition, or may select on the additional basis of a desired function e.g. to select neutralising antibodies rather than just antigen-binding antibodies, to select antibodies that can change characteristics of targeted cells, such as their signalling cascades, their shape, their growth rate, their capability of influencing other cells, their response to the influence by other cells or by other reagents or by a change in conditions, their differentiation status, etc.

The cloning step for separating individual clones from the mixture of positive cells may be carried out using limiting dilution, micromanipulation, single cell deposition by cell sorting or another method known in the art. Preferably the cloning is carried out using limiting dilution.

The methods of the invention produce immortalised B cells that produce antibodies having a desired antigen specificity. The invention thus provides an immortalised B cell clone obtainable or obtained by the methods of the invention. These B cells can be used in various ways e.g. as a source of monoclonal antibodies, as a source of nucleic acid (DNA or mRNA) encoding a monoclonal antibody of interest, for delivery to patients for cellular therapy, for research, etc.

The invention provides a composition comprising immortalised B memory lymphocytes, wherein the lymphocytes produce antibodies, and wherein the antibodies are produced at $\geq 10^N$ ng per clone per day. The invention also provides, a composition comprising clones of an immortalised B memory lymphocyte, wherein the clones produce a monoclonal antibody of interest, and wherein the antibody is produced at $\geq 10^N$ ng per clone per day. The value of N is selected from −3, −2, −1, 0, 1, 2, 3 or 4.

Antibodies of the Invention

The invention provides a monoclonal antibody obtainable or obtained from B cell clones of the invention. The invention also provides fragments of these monoclonal antibodies, particularly fragments that retain the antigen-binding activity of the antibodies.

In general, antibodies of the invention fall into two categories: they either recognise self antigens or non-self antigens. Antibodies that recognise self antigens can be used to treat diseases caused by aberrant gene expression, including cancers, and by aberrant protein processing, including Alzheimer's disease. Antibodies that recognise non-self antigens can be used to treat infectious diseases, including parasitic, viral and bacterial infections. The invention can advantageously provide human antibodies that recognise antigens of interest where it has not previously been possible.

The methods of the invention produce antibodies with the characteristics of those produced in the course of a physiological human immune response i.e. antibody specificities that can only be selected by the human immune system. This applies to the response to human pathogens including HIV, the *Plasmodium* species that cause human malaria, human hepatitis B and C viruses, Measles virus, Ebola virus, the SARS virus, Pox virus, Bunyaviridae, Arenaviridae, Bornaviridae, Reoviridae (including rotaviruses and orbiviruses), Retroviridae (including HTLV-I, HTLV-II, HIV-1, HIV-2), Polyomaviridae, Papillomaviridae, Adenoviridae, Parvoviridae, Herpesviridae (including herpes simplex viruses 1 and 2, cytomegaloviruses, varicella-zoster virus, herpesviruses 6A, 6B and 7), Poxviridae, Hepadnaviridae, etc. (for an exhaustive list see Fields et al. 1996). It also applies to antibody responses to environmental allergens generated in allergic patients, to prion proteins, to tumour antigens generated in tumour bearing patients and to self-antigens in patients with autoimmune diseases, to amyloid proteins, etc. These antibodies can be used as prophylactic or therapeutic agents upon appropriate formulation or as a diagnostic tool.

Particularly preferred monoclonal antibodies are those that have specificity for the SARS virus. Thus the invention provides a human monoclonal antibody that can neutralise the SARS coronavirus.

In relation to any particular pathogen, a "neutralising antibody" is one that can neutralise the ability of that pathogen to initiate and/or perpetuate an infection in a host. The invention provides a neutralising monoclonal human antibody, wherein the antibody recognises an antigen from a pathogen selected from: human immunodeficiency virus; hepatitis A virus; hepatitis B virus; hepatitis C virus; herpes simplex virus type 1 or type 2; SARS coronavirus; measles virus; mumps virus; rubella virus; rabies virus; ebola virus; influenza virus; papillomavirus; vaccinia virus; varicella-zoster virus; variola virus; polio virus; rhino virus; respiratory syncytial virus; *P. falciparum; P. vivax; P. malariae; P. ovale; Corynebacterium diphtheriae; Clostridium tetani; Clostridium botilinum; Bordetella pertussis; Haemophilus influenzae; Neisseria meningitidis*, serogroup A, B, C, W135 and/or Y; *Streptococcus pneumoniae; Streptococcus agalactiae; Streptococcus pyogenes; Staphylococcus aureus; Bacillus anthracis; Moraxella catarrhalis; Chlaymidia trachomatis; Chlamydia pneumoniae; Yersinia pestis; Francisella tularensis; Salmonella* species; *Vibrio cholerae*; toxic *E. coli*; a human endogenous retrovirus; etc.

The invention also provides monoclonal human antibodies that recognise proteins specifically expressed in tumours, in diseased cardiovascular cells, during inflammatory responses, in neurological disorders (including Alzheimer's disease e.g. β-amyloid proteins), in encephalopathies, etc. The invention also provides monoclonal human antibodies that recognise narcotic substances such as cocaine, heroin, benzoylecgonine, amphetamines, etc.

Specific antigens that may be recognised by antibodies of the invention include, but are not limited to: TNF-α, β-amyloid protein, SARS coronavirus spike protein, prion protein PrP, complement C5, CBL, CD147, IL-8, HIV glycoprotein gp120, VLA-4, CD11a, CD18, VEGF, CD40L, cellular adhesion molecules such as ICAMs and VCAMs, CD80, integrins, TPL2, Her2, etc.

The invention also provides an antibody having two polypeptide chains, wherein one or both of polypeptide chains has/have a human VDJ sequence.

Monoclonal antibodies produced by the methods of the invention may be further purified, if desired, using filtration, centrifugation and various chromatographic methods such as HPLC or affinity chromatography. Techniques for purification of monoclonal antibodies, including techniques for producing pharmaceutical-grade antibodies, are well known in the art.

Fragments of the monoclonal antibodies of the invention can be obtained from the monoclonal antibodies so produced by methods that include digestion with enzymes, such as pepsin or papain, and/or by cleavage of disulfide bonds by chemical reduction. Antibody "fragments" include Fab, F(ab')$_2$ and Fv fragments. The invention also encompasses single-chain Fv fragments (scFv) derived from the heavy and light chains of a monoclonal antibody of the invention e.g. the invention includes a scFv comprising the CDRs from an antibody of the invention.

The invention also provides a monoclonal human antibody with neutralising activity, wherein the antibody can neutralise at a concentration of $10^{-9}$ M or lower (e.g. $10^{-10}$ M, $10^{-11}$ M, $10^{-12}$ M or lower).

Monoclonal antibodies are particularly useful in identification and purification of the individual polypeptides or other antigens against which they are directed. The monoclonal antibodies of the invention have additional utility in that they may be employed as reagents in immunoassays, radioimmunoassays (RIA) or enzyme-linked immunosorbent assays (ELISA). In these applications, the antibodies can be labelled with an analytically-detectable reagent such as a radioisotope, a fluorescent molecule or an enzyme. The monoclonal antibodies produced by the above method may also be used for the molecular identification and characterization (epitope mapping) of antigens recognized by protected individuals in complex pathogens such as plasmodia, the isolation of cross-reactive protective antibodies in the case of highly variable pathogens such as those found in HIV and for detecting pathogens and determining their variability.

Antibodies of the invention can be coupled to a drug for delivery to a treatment site or coupled to a detectable label to facilitate imaging of a site comprising cells of interest, such as cancer cells. Methods for coupling antibodies to drugs and detectable labels are well known in the art, as are methods for imaging using detectable labels.

Antibodies of the invention may be attached to a solid support.

Antibodies of the invention are preferably provided in purified form. Typically, the antibody will be present in a composition that is substantially free of other polypeptides e.g. where less than 90% (by weight), usually less than 60% and more usually less than 50% of the composition is made up of other polypeptides.

Antibodies of the invention may be immunogenic in non-human (or heterologous) hosts e.g. in mice. In particular, the antibodies may have an idiotope that is immunogenic in non-human hosts, but not in a human host. Antibodies of the invention for human use include those that cannot be obtained from hosts such as mice goats, rabbits, rats, non-primate mammals, etc. and cannot be obtained by humanisation or from xeno-mice.

Antibodies of the invention can be of any isotype (e.g. IgA, IgG, IgM i.e. an a, y or p heavy chain), but will generally be IgG. Within the IgG isotype, antibodies may be IgG1, IgG2, IgG3 or IgG4 subclass, Antibodies of the invention may have a κ or a λ light chain.

The invention also provides an immortalised B memory lymphocyte cell (particularly a human cell), wherein the cell is infected with EBV and encodes an antibody of the invention.

Pharmaceutical Compositions

The use of monoclonal antibodies as the active ingredient of pharmaceuticals is now widespread, including the products HERCEPTIN™ (trastuzumab), RITUXAN™ (rituximab), CAMPATH™ (alemtuzumab), REMICADE™ (infliximab), REOPRO™ (abciximab), MYLOTARG™ (gemtuzumab ozogamicin), ZEVALIN™ (ibritumomab tiuxetan), Omalizumab, SYNAGIS™ (palivizumab), ZENAPAX™ (daclizumab), etc. These include antibodies that recognise human self-antigens (e.g. HERCEPTIN™ (trastuzumab) recognises the Her2 marker) and antibodies that recognise pathogenic antigens (e.g. SYNAGIS™ (palivizumab) recognises an antigen from respiratory syncytial virus).

The invention thus provides a pharmaceutical composition containing the monoclonal antibodies of the invention and/or the transformed B cells of the invention. A pharmaceutical composition may also contain a pharmaceutically acceptable carrier for administration of the antibody. The carrier should not itself induce the production of antibodies harmful to the individual receiving the composition and should not be toxic. Suitable carriers may be large, slowly metabolised macromolecules such as proteins, polypeptides, liposomes, polysaccharides, polylactic acids, polyglycolic acids, polymeric amino acids, amino acid copolymers and inactive virus particles.

Pharmaceutically acceptable salts can be used, for example mineral acid salts, such as hydrochlorides, hydrobromides, phosphates and sulphates, or salts of organic acids, such as acetates, propionates, malonates and benzoates.

Pharmaceutically acceptable carriers in therapeutic compositions may additionally contain liquids such as water, saline, glycerol and ethanol. Additionally, auxiliary substances, such as wetting or emulsifying agents or pH buffering substances, may be present in such compositions. Such carriers enable the pharmaceutical compositions to be formulated as tablets, pills, dragees, capsules, liquids, gels, syrups, slurries and suspensions, for ingestion by the patient.

Preferred forms for administration include forms suitable for parenteral administration, e.g. by injection or infusion, for example by bolus injection or continuous infusion. Where the product is for injection or infusion, it may take the form of a suspension, solution or emulsion in an oily or aqueous vehicle and it may contain formulatory agents, such as suspending, preservative, stabilising and/or dispersing agents. Alternatively, the antibody molecule may be in dry form, for reconstitution before use with an appropriate sterile liquid.

Once formulated, the compositions of the invention can be administered directly to the subject. It is preferred that the compositions are adapted for administration to human subjects.

The pharmaceutical compositions of this invention may be administered by any number of routes including, but not limited to, oral, intravenous, intramuscular, intra-arterial, intramedullary, intraperitoneal, intrathecal, intraventricular, transdermal, transcutaneous (e.g. WO98/20734), topical, subcutaneous, intranasal, enteral, sublingual, intravaginal or rectal routes. Hyposprays may also be used to administer the pharmaceutical compositions of the invention. Typically, the therapeutic compositions may be prepared as injectables, either as liquid solutions or suspensions. Solid forms suitable for solution in, or suspension in, liquid vehicles prior to injection may also be prepared.

Direct delivery of the compositions will generally be accomplished by injection, subcutaneously, intraperitoneally, intravenously or intramuscularly, or delivered to the interstitial space of a tissue. The compositions can also be administered into a lesion. Dosage treatment may be a single dose schedule or a multiple dose schedule. Known antibody-based pharmaceuticals provide guidance relating to frequency of administration e.g. whether a pharmaceutical should be delivered daily, weekly, monthly, etc. Frequency and dosage may also depend on the severity of symptoms.

It will be appreciated that the active ingredient in the composition will be an antibody molecule. As such, it will be susceptible to degradation in the gastrointestinal tract. Thus, if the composition is to be administered by a route using the gastrointestinal tract, the composition will need to contain agents which protect the antibody from degradation but which release the antibody once it has been absorbed from the gastrointestinal tract.

A thorough discussion of pharmaceutically acceptable carriers is available in Remington's Pharmaceutical Sciences (Mack Publishing Company, N.J. 1991) and in Gennaro (2000) *Remington: The Science and Practice of Pharmacy*, 20th edition, ISBN: 0683306472.

Pharmaceutical compositions of the invention generally have a pH between 5.5 and 8.5, preferably between 6 and 8, and more preferably about 7. The pH may be maintained by the use of a buffer. The composition may be sterile and/or pyrogen free. The composition may be isotonic with respect to humans. Pharmaceutical compositions of the invention are preferably supplied in hermetically-sealed containers.

Pharmaceutical compositions will include an effective amount of one or more antibodies of the invention and/or one or more transformed B cells of the invention i.e. an amount that is sufficient to treat, ameliorate, or prevent a desired disease or condition, or to exhibit a detectable therapeutic effect. Therapeutic effects also include reduction in physical symptoms. The precise effective amount for any particular subject will depend upon their size and health, the nature and extent of the condition, and the therapeutics or combination of therapeutics selected for administration. The effective amount for a given situation is determined by routine experimentation and is within the judgment of a clinician. For purposes of the present invention, an effective dose will generally be from about 0.01 mg/kg to about 50 mg/kg, or about 0.05 mg/kg to about 10 mg/kg of the compositions of the present invention in the individual to which it is administered. Known antibody-based pharmaceuticals provide guidance in this respect e.g. HERCEPTIN™ (trastuzumab) is administered by intravenous infusion of a 21 mg/ml solution, with an initial loading dose of 4 mg/kg body weight and a weekly maintenance dose of 2 mg/kg body weight; RITUXAN™ (rituximab) is administered weekly at 375 mg/m$^2$; etc.

Compositions can include more than one (e.g. 2, 3, 4, 5, etc.) antibody of the invention, particularly where such antibodies bind to different antigens (or to different epitopes in the same antigen) to provide a synergistic therapeutic effect.

Antibodies of the invention may be administered (either combined or separately) with other therapeutics e.g. with chemotherapeutic compounds, with radiotherapy, etc.

In compositions of the invention that include antibodies of the invention, the antibodies preferably make up at least 50% by weight (e.g. 60%, 70%, 80%, 90%, 95%/O, 97%, 98%, 99% or more) of the total protein in the composition. The antibodies are thus in purified form.

The invention provides a method of preparing a pharmaceutical, comprising the steps of: (i) preparing a monoclonal antibody of the invention; and (ii) admixing the purified antibody with one or more pharmaceutically-acceptable carriers.

The invention also provides a method of preparing a pharmaceutical, comprising the step of admixing a monoclonal antibody with one or more pharmaceutically-acceptable carriers, wherein the monoclonal antibody is a monoclonal antibody that was obtained from a transformed B cell of the invention. Thus the procedures for first obtaining the monoclonal antibody and then preparing the pharmaceutical can be performed at very different times by different people in different places (e.g. in different countries).

As an alternative to delivering monoclonal antibodies or B cells for therapeutic purposes, it is possible to deliver nucleic acid (typically DNA) to a subject that encodes the monoclonal antibody (or active fragment thereof) of interest, such that the nucleic acid can be expressed in the subject in situ to provide a desired therapeutic effect. Suitable gene therapy and nucleic acid delivery vectors are known in the art.

Medical Treatments and Uses

The monoclonal antibodies of the invention or fragments thereof may be used for the treatment of disease, for the prevention of disease or for the diagnosis of disease. Preferably, the monoclonal antibodies of the invention are used for the prevention or treatment of SARS or for the diagnosis or SARS. Methods of diagnosis may include contacting an antibody or an antibody fragment with a sample. The methods of diagnosis may also include the detection of an antigen/antibody complex.

The invention provides a composition of the invention for use as a medicament. It also provides the use of an antibody of the invention in the manufacture of a medicament for treatment of a patient and/or diagnosis in a patient. It also provides a method for treating a subject and/or of performing diagnosis on a subject, comprising the step of administering to them a composition of the invention. The subject is preferably a human. One way of checking efficacy of therapeutic treatment involves monitoring disease symptoms after administration of the composition of the invention. Treatment can be a single dose schedule or a multiple dose schedule. The invention is useful for treating infectious diseases, cancers, inflammatory diseases, autoimmune diseases, etc.

Antibodies of the invention can be used in passive immunisation.

Compositions of the invention will generally be administered directly to a patient. Direct delivery may be accomplished by parenteral injection (e.g. subcutaneously, intraperitoneally, intravenously, intramuscularly, or to the interstitial space of a tissue), or by rectal, oral (e.g. tablet, spray), vaginal, topical, transdermal or transcutaneous, intranasal, ocular, aural, pulmonary or other mucosal administration.

Compositions of the invention may be prepared in various forms. For example, the compositions may be prepared as injectables, either as liquid solutions or suspensions. Solid forms suitable for solution in, or suspension in, liquid vehicles prior to injection can also be prepared (e.g. a lyophilised composition, like SYNAGIS™ (palivizumab) and HERCEPTIN™ (trastuzumab), for reconsitution with sterile water containing a preservative). The composition may be prepared for topical administration e.g. as an ointment, cream or powder. The composition may be prepared for oral administration e.g. as a tablet or capsule, as a spray, or as a syrup (optionally flavoured). The composition may be prepared for pulmonary administration e.g. as an inhaler, using a fine powder or a spray. The composition may be prepared as a suppository or pessary. The composition may be prepared for nasal, aural or ocular administration e.g. as drops. The composition may be in kit form, designed such that a combined composition is reconstituted just prior to administration to a patient. For example, a lyophilised antibody can be provided in kit form with sterile water or a sterile buffer.

Antibodies and fragments thereof as described in the present invention may also be used in a kit for the diagnosis of tumour, autoimmune or allergic disease.

Recombinant Expression

The immortalised memory B lymphocytes produced using the method of the invention may also be used as a source of nucleic acid for the cloning of antibody genes for subsequent recombinant expression. Expression from recombinant sources is more common for pharmaceutical purposes than expression from B cells or hybridomas e.g. for reasons of stability, reproducibility, culture ease, etc.

Thus the invention provides a method for preparing a recombinant cell, comprising the steps of: (i) preparing an immortalised B cell clone as described above; (ii) obtaining one or more nucleic acids (e.g. heavy and/or light chain genes) from the B cell clone that encodes the antibody of interest; and (iii) inserting the nucleic acid into an expression host in order to permit expression of the antibody of interest in that host.

Similarly, the invention provides a method for preparing a recombinant cell, comprising the steps of: (i) preparing an immortalised B cell clone as described above; (ii) sequencing nucleic acid(s) from the B cell clone that encodes the antibody of interest; and (iii) using the sequence information from step (ii) to prepare nucleic acid(s) for inserting into an expression host in order to permit expression of the antibody of interest in that host.

The invention also provides a method of preparing a recombinant cell, comprising the step of transforming a host cell with one or more nucleic acids that encode a monoclonal antibody of interest, wherein the nucleic acids are nucleic acids that were derived from an immortalised B cell clone of the invention. Thus the procedures for first preparing the nucleic acid(s) and then using it to transform a host cell can be performed at different times by different people in different places (e.g. in different countries).

These recombinant cells of the invention can then be used for expression and culture purposes. They are particularly useful for expression of antibodies for large-scale pharmaceutical production. They can also be used as the active ingredient of a pharmaceutical composition. Any suitable culture techniques can be used, including but not limited to static culture, roller bottle culture, ascites fluid, hollow-fiber type bioreactor cartridge, modular minifermenter, stirred tank, microcarrier culture, ceramic core perfusion, etc.

Methods for obtaining and sequencing immunoglobulin genes from B cells are well known in the art e.g. see chapter 4 of *Kuby Immunology* (4th edition, 2000; ASIN: 0716733315).

The expression host is preferably a eukaryotic cell, including yeast and animal cells, particularly mammalian cells (e.g. CHO cells, human cells such as PER.C6 [Crucell; Jones et al. *Biotechnol Prog* 2003, 19(1):163-8] or HKB-11 [Bayer; Cho et al. *Cytotechnology* 2001, 37:23-30; Cho et al. *Biotechnol Prog* 2003, 19:229-32] cells, myeloma cells [U.S. Pat. Nos. 5,807,715 and 6,300,104], etc.), as well as plant cells. Preferred expression hosts can glycosylate the antibody of the invention, particularly with carbohydrate structures that aye not themselves immunogenic in humans. Expression hosts that can grow in serum-free media are preferred. Expression hosts that can grow in culture without the presence of animal-derived products are preferred.

The expression host may be cultured to give a cell line.

The invention provides a method for preparing one or more nucleic acid molecules (e.g. heavy and tight chain genes) that encodes an antibody of interest, comprising the steps of: (i) preparing an immortalised B cell clone according to the invention; (ii) obtaining from the B cell clone nucleic acid that encodes the antibody of interest. The invention also provides a method for obtaining a nucleic acid sequence that encodes an antibody of interest, comprising the steps of: (i) preparing an immortalised B cell clone according to the invention; (ii) sequencing nucleic acid from the B cell clone that encodes the antibody of interest.

The invention also provides a method of preparing nucleic acid molecule(s) that encodes an antibody of interest, comprising the step of obtaining the nucleic acid from a B cell clone that was obtained from a transformed B cell of the invention. Thus the procedures for first obtaining the B cell clone and then preparing nucleic acid(s) from it can be performed at very different times by different people in different places (e.g. in different countries).

The invention provides a method for preparing an antibody (e.g. for pharmaceutical use), comprising the steps of: (i) transforming a population of human B memory lymphocytes and selecting a transformed B cell that produces an antibody with a desired specificity, as described above; (ii) obtaining and/or sequencing one or more nucleic acids (e.g. heavy and light chain genes) from the selected B cell the antibody of interest; (iii) inserting the nucleic acid(s) into or using the nucleic acid(s) to prepare an expression host that can express the antibody of interest; (iv) culturing or sub-culturing the expression host under conditions where the antibody of interest is expressed; and, optionally, (v) purifying the antibody of the interest.

The invention also provides a method of preparing an antibody comprising the steps of: culturing or sub-culturing an expression host cell population under conditions where the antibody of interest is expressed and, optionally, purifying the antibody of the interest, wherein said expression host cell population has been prepared by (i) providing nucleic acid(s) encoding a selected B cell the antibody of interest that is produced by a population of B memory lymphocytes prepared as described above, (ii) inserting the nucleic acid(s) into an expression host that can express the antibody of interest, and (iii) culturing or sub-culturing expression hosts comprising said inserted nucleic acids to produce said expression host cell population. Thus the procedures for first preparing the recombinant expression host and then culturing it to express antibody can be performed at very different times by different people in different places (e.g. in different countries).

The invention also provides a method of preparing a pharmaceutical, comprising the step of admixing a monoclonal antibody with one or more pharmaceutically-acceptable carriers, wherein the monoclonal antibody is a monoclonal antibody that was obtained from an expression host of the invention. Thus the procedures for first obtaining the monoclonal antibody (e.g. expressing it and/or purifying it) and then admixing it with the pharmaceutical carrier(s) can be performed at very different times by different people in different places (e.g. in different countries).

Starting with a transformed B cell of the invention, various steps of culturing, sub-culturing, cloning, sub-cloning, sequencing, nucleic acid preparation etc. can be performed in order to perpetuate the antibody expressed by the transformed B cell, with optional optimisation at each step. In a preferred embodiment, the above methods further comprise techniques of optimisation (e.g. affinity maturation or optimisation) applied to the nucleic acids encoding the antibody. The invention encompasses all cells, nucleic acids, vectors, sequences, antibodies etc. used and prepared during such steps.

In all these methods, the nucleic acid used in the expression host may be manipulated between steps (ii) and (iii) to insert, delete or amend certain nucleic acid sequences. Changes from such manipulation include, but are not limited to, changes to introduce restriction sites, to amend codon usage, to add or optimise transcription and/or translation regulatory sequences, etc. It is also possible to change the nucleic acid to alter the encoded amino acids. For example, it may be useful to introduce one or more (e.g. 1, 2, 3, 4, 5, 6, 7, 8, 9, 10, etc.) amino acid substitutions, one or more (e.g. 1, 2, 3, 4, 5, 6, 7, 8, 9, 10, etc.) amino acid deletions and/or one or more (e.g. 1, 2, 3, 4, 5, 6, 7, 8, 9, 10, etc.) amino acid insertions into the antibody's amino acid sequence. Such point mutations can modify effector functions, antigen-binding affinity, post-translational modifications, immunogenicity, etc., can introduce amino acids for the attachment of covalent groups (e.g. labels) or can introduce tags (e.g. for purification purposes). Mutations can be introduced in specific sites or can be introduced at random, followed by selection (e.g. molecular evolution).

SARS

Antibodies specific for the SARS virus may be particularly useful for prophylaxis and may be administered to health care workers or other people who may come into contact with SARS virus infected patients. Such passive serotherapy may offer an immediate cure of infected individuals as well as containment through protection of contacts and medical personnel. Human sera containing antibodies to the SARS virus are not available in sufficient amounts, therefore the method of the invention provides an ideal way of producing human neutralizing monoclonal antibodies. Such antibodies may be used to develop a passive serotherapy against this and other pathogens.

The invention therefore also provides a method of preventing transmission of the SARS virus comprising administering an effective amount of an antibody or antibody fragment specific for the SARS virus. Stocks of antibody specific for the SARS virus should therefore be maintained so that they are available for immediate use in any further SARS outbreak.

Non-Human Species

The invention has been described above in relation to human antibodies prepared from human B cells. It will be appreciated that the invention is not technically restricted to use with human cells, and can be used with any organism of interest e.g. to provide antibodies for therapeutic or diagnostic veterinary use. Organisms with B cells that can be transformed by the methods of the invention include primates (monkeys, apes, gorillas, gibbons, lemurs, chimpanzees, baboons, orang-utans, macaques, etc.) cows, horses, goats, sheep, pigs, dogs, cats, camels, sharks, fish, etc.

General

The term "comprising" encompasses "including" as well as "consisting" e.g. a composition "comprising" X may consist exclusively of X or may include something additional e.g. X+Y.

The word "substantially" does not exclude "completely" e.g. a composition which is "substantially free" from Y may be completely free from Y. Where necessary, the word "substantially" may be omitted from the definition of the invention.

The term "about" in relation to a numerical value x means, for example, x±10%.

BRIEF DESCRIPTION OF DRAWINGS

FIG. 3 shows clonal analysis of the human antibody response to the SARS virus spike protein. Culture supernatants were tested for their capacity to stain BHK cells transfected with SARS virus spike protein mRNA (Frankfurt isolate) and for their capacity to neutralize the same strain of SARS virus.

MODES FOR CARRYING OUT THE INVENTION

The present invention permits the cloning of human memory B lymphocytes with very high efficiency and achieves this by the combination of two stimuli, namely:

EBV, that immortalizes human B cells with low efficiency and a polyclonal B cell activator that enhances the efficiency of EBV-immortalization.

Example 1

Cloning of B Cells

Human memory B cells (CD19$^+$ CD27$^+$ IgM$^-$ IgD$^-$) were isolated from healthy donors by cell sorting using methods well known in the art. Different numbers of cells were seeded in replicate cultures in 96 well microplates in the presence of irradiated mononuclear cells (5×10$^5$/ml) and either E13V (supernatant of B95-8 cells) alone or EBV in combination with CpG 2006 (2.5 μg/ml) and recombinant IL-2 (1000 U/ml). After 15 days the percentage of cultures containing growing cells was scored. Frequencies were determined by limiting dilution assays. Cultures were scored for growing cells. Cloning efficiency using four different sources of B cells were as follows:

|  | Cloning efficiency | |
| --- | --- | --- |
| B cell source | EBV | EBV + CpG + IL-2 |
| Exp 1 (CD19$^+$ CD27$^+$ IgM$^-$ IgD$^-$) | 1 in 200 | 1 in 1 |
| Exp 2 (CD19$^+$ CD27$^+$ IgM$^-$ IgD$^-$) | 1 in 120 | 1 in 1.5 |
| Exp 3 (CD19$^+$ CD27$^+$ IgM$^-$ IgD$^-$) | 1 in 60 | 1 in 1 |
| Exp 4 (CD19$^+$ CD27$^+$) | 1 in 90 | 1 in 1.6 |

No growth was observed in the absence of EBV.

Thus the methods of the invention allow virtually every human memory B cell to be cloned (efficiency close to 100%4). The method is also suitable for subcloning.

Example 2

Production of Antibodies with a Desired Specificity

In a further experiment it was demonstrated that the immortalisation can be used to exploit immunological memory to produce human monoclonal antibodies of the desired specificity.

Mononuclear cells were isolated from 20 ml peripheral blood obtained from a healthy blood donor. CD19$^+$CD27$^+$ IgG$^+$ human memory B cells were isolated by cell sorting and seeded at 10 cells/well in 96 well microplates in the presence of EBV, CpG 2006 (2.5 μg/ml), recombinant IL-2 (1000 U/ml) and irradiated mononuclear cells (5×105/ml). Seeding only 10 cells per well helps to increase cloning efficiency. After 15 days all cultures contained growing cells. A sample of supernatant was collected and tested in ELISA for total IgG antibodies and for IgG specific for *Toxoplasma gondii*, tetanus toxoid and measles virus. The supernatants were also tested in a measles virus neutralization assay using Vero cells as targets.

Some of the positive cultures identified were subcloned by limiting dilution to isolate specific clones producing the desired monoclonal antibody. Cultures were subcloned at 0.5 cells/well in the presence of CpG 2006 (2.5 μg/ml), IL-2 (1000 U/ml) and irradiated PBMC (5×10$^5$/ml).

| Antibody (detection method) | Positive cultures [#] | Specific clones isolated/ attempts made [*] |
| --- | --- | --- |
| IgG (ELISA) | 180/180 |  |
| Anti-*Toxoplasma gondii* (ELISA) | 23/180 | 5/6 |
| Anti-tetanus toxoid (ELISA) | 19/180 | 5/6 |
| Anti-Measles virus (ELISA) | 36/180 | 7/9 |
| Anti-Measles virus (neutralization) | 7/180 | 4/4 |

[#] For ELISA, number of cultures with OD >0.8 in an assay with background <0.2; for neutralisation assay, number with complete protection from cytolitic effect of measles virus
[*] Number of cases where at least one antigen-specific clone could be isolated, relative to the number of original cultures that were cloned. Cloning efficiency varied from 50 to 100%.

EBV-transformed B cell clones that produce IgG antibodies to measles virus, tetanus toxoid and *Toxoplasma gondii* could thus be isolated, showing that human monoclonal antibodies with multiple memory specificities can be prepared from a small sample of human peripheral blood.

Example 3

Immortalised Memory B Cells that Express Antibodies Specific for SARS Coronavirus Blood samples were obtained from two patients with a clinical record of SARS. Both patients had serum anti-SARS antibodies as detected by two assays: (i) a neutralization assay which detects neutralizing antibodies directed against surface proteins of the SAGS virus, likely the spike protein and (ii) an ELISA assay, that detects antibodies binding to any denatured protein of the SARS virus.

For the neutralization assay, serial dilutions of serum obtained from the blood were added to microplate wells containing Vero cells, followed by titrated amounts of SARS virus. After 2 days, the cytopathic effect was recorded by visual inspection. A conventional ELISA was also developed using SARS virus infected Vero cells lysed in 3% SDS as the antigen.

For the production of the clone of B cells producing monoclonal antibodies specific for the SARS virus, blood from the patient showing the higher titer of binding and neutralizing antibodies was selected.

Memory B cells carrying surface IgG were isolated using anti-human IgG microbeads, incubated with EBV (50% supernatant of B95-8 cells) for 6 hours and were then plated at 10 cells/well in 96 well microplates in the presence of 2.5 μg/ml CpG 2006 and allogeneic irradiated PBMC (in these experiments IL-2 was omitted). After two weeks the culture supernatants were screened for the presence of specific antibodies.

Figure 1:
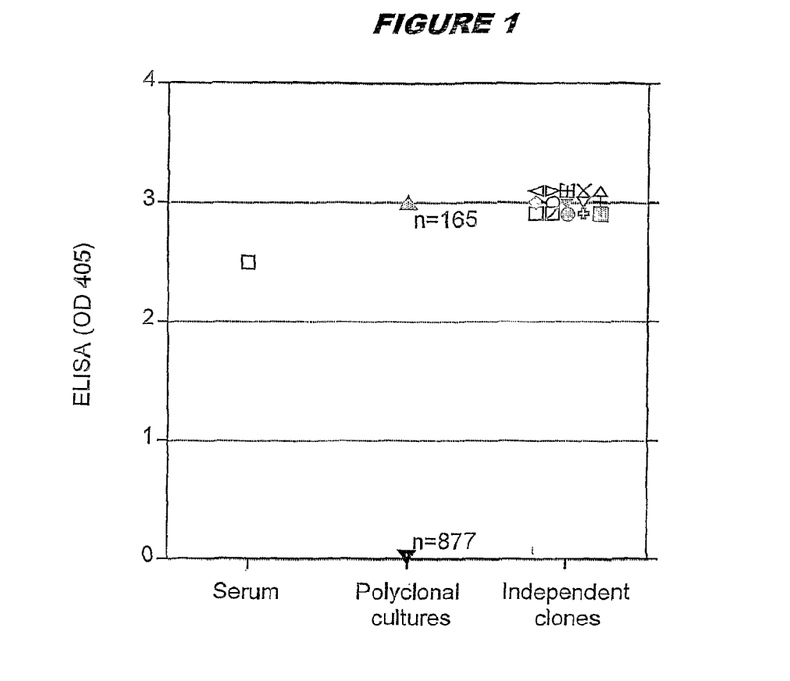
FIG. 1 shows results of the ELISA using SARS virus-infected Vero cells lysed in 3% SDS as antigen. Shown are the OD values of serum (1/5000 dilution), supernatants of polyclonal cultures and of independent B cell clones (1/2 dilution).

Out of 1042 culture supernatants tested, 165 scored positive in the ELISA assay (FIG. 1). 23 of these cultures were cloned as above and specific clones were isolated from 16 of them. Some of the human monoclonal antibodies isolated recognise the nucleoprotein of the SARS virus in western blots, while some do not, suggesting that they may recognise different viral proteins (data not shown). None of these antibodies showed neutralizing activity.

Figure 2:
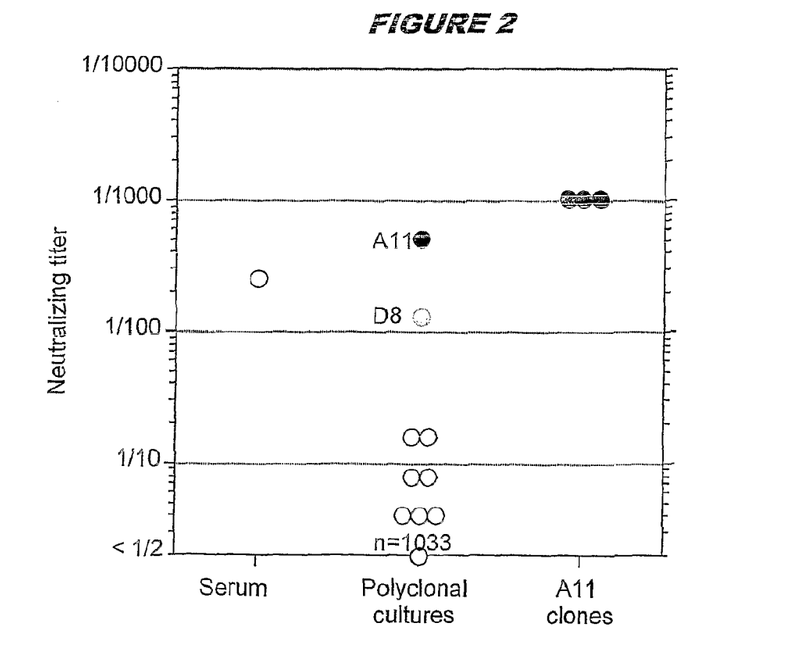
FIG. 2 shows the neutralizing titer of antibodies specific for the SARS virus. From left to right: neutralization titer (Vero cell assay) of convalescent serum; supernatants of polyclonal cultures; positive clones isolated from the culture with highest neutralizing titer.

Out of 1042 culture supernatants tested in the neutralization assay, seven showed low level neutralizing activity while two (A11 and D8) showed high neutralizing titer (1/512 and 1/256 respectively). The A11 culture was cloned by limiting dilution in the presence of CpG and irradiated PBMC and several B cell clones with comparably high neutralizing activity were isolated (FIG. 2). The A11 antibodies did not bind in the ELISA assay, but stained surface spikes of the SARS virus as detected by electron microscopy (data not shown).

Therefore, using this method it is possible to produce neutralizing antibodies specific for an antigen using only a small blood sample (around 10 ml) within a short timespan (30-40 days). The method also allows selection of the best antibody from a large pool, and is therefore a high throughput method.

The anti-SARS antibodies neutralise the SARS virus at concentrations of 5 ng/ml. Neutralization of respiratory syncytial virus (RSV, a common cause of respiratory tract infections, especially in children) by commercially available humanized antibodies produced by conventional techniques requires around a 1000-fold higher antibody concentration (Johanson et al. 1997). Therefore the fully human antibodies produced by the method of the invention appear to be around 1000-fold more effective. This suggests that very small amounts of the antibody described here should be sufficient to prevent or cure SARS infection.

Example 4

Screening SARS Virus Convalescent Patients for Antibodies

Peripheral blood was obtained from a patient at different times after acute infection with SARS virus (2, 4 and 6 months after infection). PBMC were isolated by gradient centrifugation. IgG+ memory B cells were isolated by an improved method that avoids triggering of the B cell receptor. Total B cells were isolated from PBMC using CD22 microbeads (Miltenyi), which were found to be even better than using CD19 microbeads. The cells were stained with antibodies to human IgM, IgD and IgA and negative cells carrying surface IgG were isolated by cell sorting. B cells were pulsed with EBV (50% supernatant of B-95-8 cells) for 8 hours and then plated at 10 cells/well in 96 well U-bottom microplates in complete RPMI medium supplemented with 10% FCS, 2.51 g/ml CpG 2006 and irradiated PBMC ($2 \times 10^5$/ml). In this experiment IL-2 was not used. After 2 weeks the culture supernatants were screened for the presence of specific antibodies using the three assays described below. Positive cultures were cloned by limiting dilution in the presence of CpG 2006 and irradiated PBMC as above. Positive clones were expanded and the antibody produced was purified from culture supernatants by affinity chromatography on protein A columns (Amersham).

The Frankfurt isolate of the SARS virus (Genbank accession number AY310120) was used for three in vitro assays:

ELISA Vero cells were infected at a multiplicity of infection of 0.01 plaque forming units per cell. Cell culture supernatant collected after 2 days was cleared by centrifugation at 3000 rpm, 5 min. The supernatant was subjected to centrifugation at 20,000 rpm for 2 hours in a Beckman SW28 rotor through a 20% sucrose cushion. The pellet was purified using a potassium tartrate/glycerol gradient and resuspended in 500 µl TNE buffer (10 mM Tris-HCl, pH 7.4, 0.15 M NaCl, 2 ml EDTA) to a protein concentration of approx 0.5 mg/ml. The antigen suspension used for the ELISA assay was prepared by adding 1% SDS to the viral pellet followed by boiling for 10 min. ELISA plates were coated with a 1:1000 dilution of SARS virus antigen in 0.1 M phosphate buffer. Dilutions of sera or culture supernatant were added and specific IgG1 antibodies were detected using alkaline phosphatase goat anti-human IgG. Results were expressed in arbitrary units (AU) relative to the 2 month sample (=1000 AU). Sera from 20 normal donors tested were negative (<1 AU).

Staining Antibodies specific for native spike protein of SARS virus were detected by flow cytometry. Briefly, the SARS virus spike gene was cloned in an appropriate vector and mRNA was transcribed in vitro and used to transfect BHK cells by electroporation. Transfectants were incubated with culture supernatants or serum, washed and stained with APC-labelled goat anti-human IgG antibody. This assay detects IgG1 antibodies directed against native spike antigen, most of which have neutralizing activity. Results were expressed in arbitrary units (AU) relative to the 2 month sample (=1000 AU). Sera from 20 normal donors tested were negative (<1 AU).

In vitro neutralization Sera or culture supernatants were diluted in log 2 steps and mixed with 75 $TCID_{50}$ SARS virus in 25 µl (virus titer was determined according to the method of Karber) The mixture was incubated for 45 min at room temperature. Subsequently, 50 µl trypsinized Vero cells ($1.5 \times 10^5$ per ml) were added and incubated for 3 days at 37° C. and finally, the neutralization titer was determined by visual inspection to give the serum dilution that neutralizes 75 $TCID_{50}$ SARS virus. The assays were performed in a biosafety level 4 laboratory.

Results were as follows:

| Months after infection | Anti-SARS antibody detected by | | |
|---|---|---|---|
| | ELISA | Spike staining | Neutralization |
| 2 | 1000 | 1000 | 1/128 |
| 4 | 650 | 700 | 1/128 |
| 6 | 300 | 400 | 1/128 |

While normal sera were negative, the patient's serum collected at different time points after the onset of acute disease scored positive in the three assays. Antibodies detected by ELISA and those staining spike-transfected cells were highest 2 months after infection and decreased to about one third by six months. In contrast neutralizing antibodies remained constant with a titer of 1/128. The isotype of the antibodies detected in the Spike-binding and ELISA assays was exclusively Ig1, no IgA or IgM antibodies being detected (data not shown). Thus the post-infection serum of this person had moderate titers of neutralizing antibodies to the SARS virus and IgG antibodies that bound spike proteins and detected denatured antigens in ELISA.

Example 5

Kinetics and Frequencies of Specific Memory B Cells

IgG+ memory B lymphocytes from the 2-month, 4-month and 6-month post-SARS sera were immortalized with EBV under conditions where the number of B cells per culture was limiting, as described above (10 B cells per well). This strategy allows analysis of the product of only a few memory B cells per culture, thus ensuring that the specific antibody detected in positive cultures is monoclonal and, at the same time, increasing the probability of isolating a clone producing the desired antibody by limiting dilution. After two weeks of culture in the presence of EBV, CpG 2006 and irradiated feeder cells the culture supernatants were screened for the presence of specific IgG antibodies using ELISA or staining of spike transfectants. The frequency of cultures screening positive in the SARS virus ELISA assay or staining SARS virus spike transfectants were as follows:

| | Positive cultures/total cultures screened (%) | |
|---|---|---|
| Months after infection | ELISA | Spike staining |
| 2 | 275/480 (57.3%) | Not determined |
| 4 | 123/480 (25.6%) | 12/576 (2.1%) |
| 6 | 44/480 (9/2%) | 21/768 (2.7%) |

The frequency of cultures producing antibodies detected by the ELISA assay was very high 2 months after infection and decreased by 4 and 6 months. The frequency of cultures producing antibodies against native spike protein measured at 4 and 6 months was lower. Importantly, the culture that scored positive for ELISA antibodies were distinct from those containing antibodies to the spike indicating that the two assays detect distinct non-overlapping antibody specificities. Furthermore, a sizeable proportion of IgG$^+$ memory B cells are specific for the spike protein.

Figure 3A:
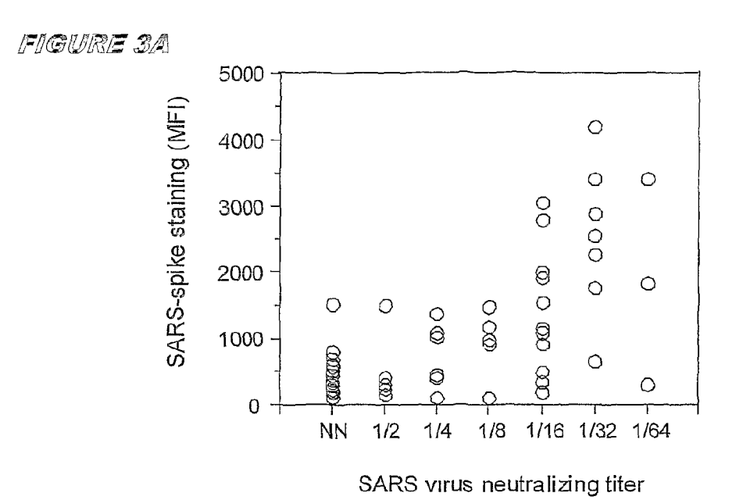
FIG. 3A, shows the correlation between neutralizing titer and staining of spike protein by undiluted culture supernatant.
Figure 3B:
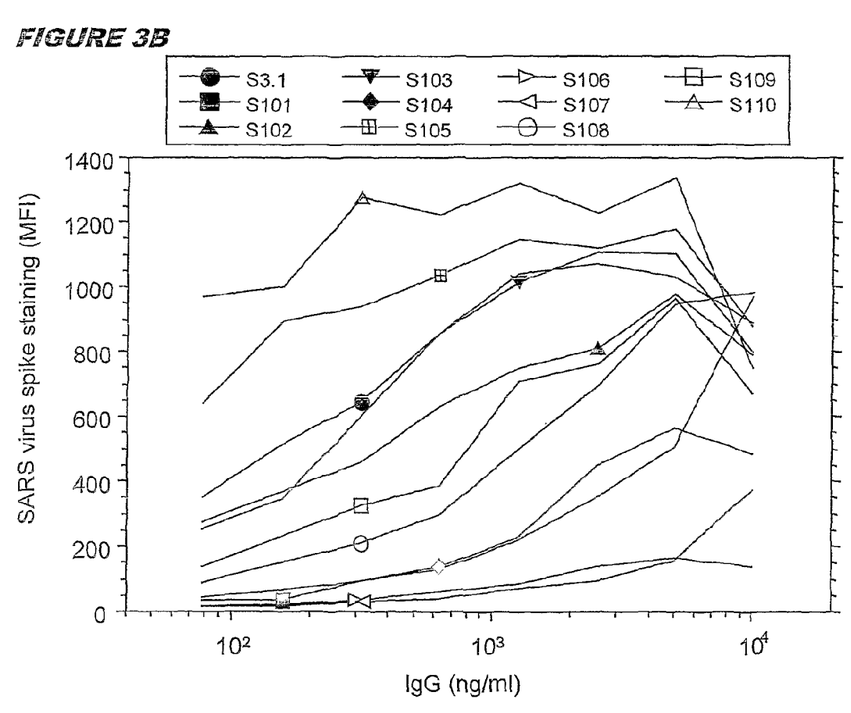
FIG. 3B shows staining of spike-transfected BHK cells by serial dilutions of supernatants from eleven neutralizing cultures, with filled symbols showing the maximum dilution where complete neutralization was observed.

Tests were then carried out to see whether there is a correlation between spike binding and neutralizing activity. 56 culture supernatants which stained spike-transfected cells were tested for their capacity to neutralize the same SARS virus isolate from which the spike protein was cloned (FIG. 3A). Although the antibodies with the highest staining showed high neutralizing titers, there were some antibodies that neutralized efficiently in spite of poor staining while others stained spike transfectants, but failed to neutralize. Furthermore, when 11 supernatants with high neutralizing titer were analyzed, no clear correlation between staining and neutralization was evident (FIG. 3B). Taken together these results indicate that at the clonal level the response to spike is heterogeneous and that not all the anti-spike antibodies produced in the course of the natural infection are capable of neutralizing the virus.

Example 6

Isolation of Monoclonal Antibodies to SARS Virus

The results shown above prove that it is possible to interrogate the human B cell memory repertoire with a variety of assays to identify cultures producing an antibody of the desired specificity. In these experiments, 29 of 38 attempts (76%) at cloning positive cultures led to the isolation of one or more clones producing antibodies of the selected specificity. The EBV clones were stable and monoclonal antibodies were recovered in the culture supernatant at concentrations of 10-20 μg/ml. Of these 29, 21 were positive in the ELISA assay and 8 were both positive in the spike staining assay and were able to neutralize SARS virus.

Out of the 21 independent clones that scored positive in the ELISA assay, 13 (62%) produced antibodies specific for the SARS virus nucleoprotein (NP) as detected by Western blot, while 5 did not recognize NP, but stained SARS virus infected cells, and the remaining 3 reacted only in the ELISA assay. As expected, none of these antibodies showed neutralizing activity.

Figure 4:
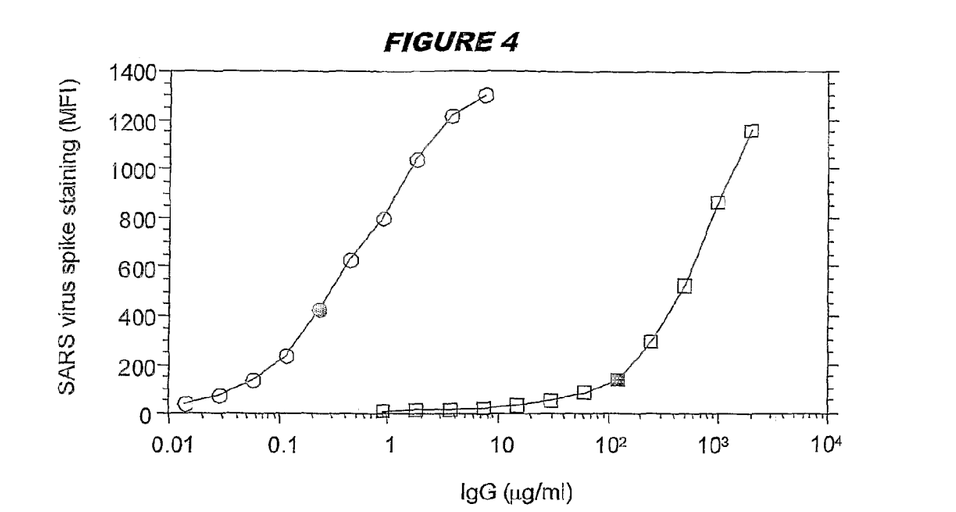
FIG. 4 shows the characterization of the SARS neutralizing antibody S3.1. Staining of spike-transfected BHK cells by purified S3.1 (circles) and 6 months convalescent serum (squares). The filled symbols indicate the maximum dilution where complete neutralization was observed.
Figures 5, 5A, 5H:
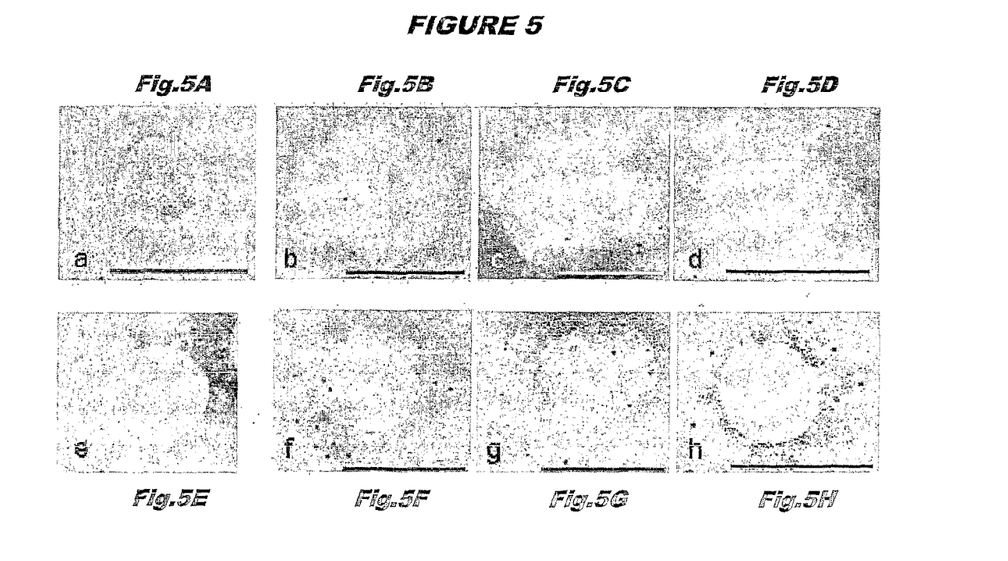
FIG. 5 shows immunoelectron microscopy of SARS coronavirus in the presence of S3.1 antibody.
Figure 6:
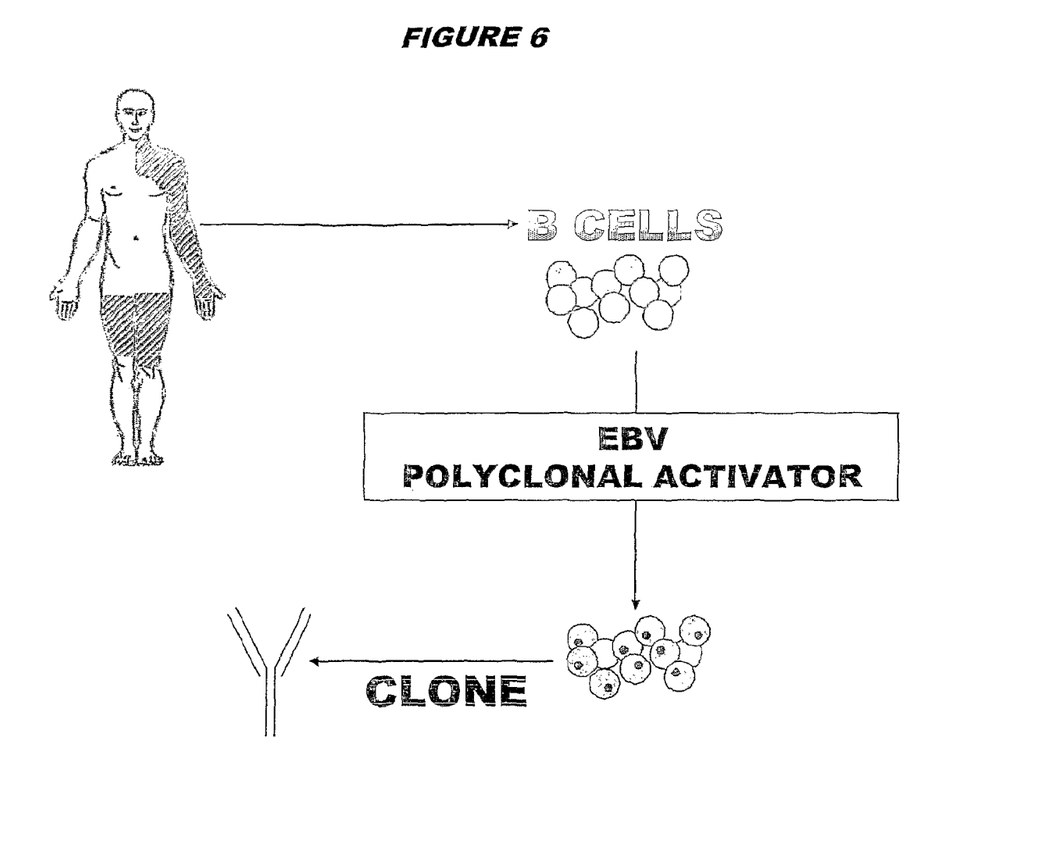
FIG. 6 is an overview of a method of the invention, from human to monoclonal antibody.

Out of the 8 independent clones staining spike transfectants and neutralizing SARS virus, one (S3.1, IgG1κ) was selected for in vivo neutralization assays. The monoclonal antibody from this clone was purified from the culture supernatant and tested for its capacity to stain spike-transfected cells and to neutralize SARS virus (FIG. 4). S3.1 neutralized 75 TCID$_{50}$ SARS virus at concentrations of ~300 ng/ml, and was up to 300 fold more potent than convalescent serum. Furthermore S3.1 neutralized the Frankfurt and Urbani isolates with the same efficiency (data not shown), and decorated the spikes of SARS-CoV as detected by immunoelectron microscopy (FIG. 5).

Example 7

S3.1 Neutralizes SARS Infection in an Animal Model

The in vivo neutralizing activity of the S3.1 monoclonal antibody was tested in a mouse model of acute SARS infection. Purified antibody was transferred to naïve mice by intraperitoneal injection to determine whether antibody alone could prevent replication of SARS virus in the respiratory tract.

Drs. L. J. Anderson and T. G. Ksiazek from the Centers for Disease Control and Prevention (CDC), Atlanta, Ga., provided SARS virus (Urbani strain) for use in an in vivo neutralization assay. The virus was isolated and passaged twice in Vero E6 cells at the CDC and was passaged in Vero cells for two additional passages in our laboratory to generate a virus stock with a titer of $10^{6.5}$ TCID$_{50}$/ml. The Vero cells were maintained in OptiPro SFM (Invitrogen). All work with infectious virus was performed inside a biosafety cabinet, in a biosafety containment level 3 facility and personnel were powered air purifying respirators (3M HEPA AirMate, Saint Paul, Minn.). The mouse studies were approved by the NIH Animal Care and Use Committee and were carried out in an approved animal biosafety level 3 facility. All personnel entering the facility wore powered air purifying respirators.

Four-to-six week-old female BALB/c mice purchased from Taconic (Germantown, N.Y.) were housed, 4 mice per cage. On day 0 mice, lightly anesthetized with is isoflurane, were injected intraperitoneally with 3 different doses (800, 200, 50 μg) of S3.1 antibody in 500 μl or with the same volume of a polyclonal human Ig that lacks neutralizing activity. 24 hours later mice were intranasally challenged with $10^4$ TCID$_{50}$ of SARS coronavirus. After two additional days mice were sacrificed and their lungs and nasal turbinates were removed and homogenized in a 5% w/v suspension in Leibovitz 15 medium (Invitrogen). Tissue samples were assessed for infection, and virus titers were determined as described above. Virus titers were expressed as log$_{10}$ TCID$_{50}$ per gram of tissue:

| | Virus replication in challenged mice | | | |
|---|---|---|---|---|
| | Lungs | | Nasal turbinates | |
| Antibody | Number infected | Mean (±SE) virus titer | Number infected | Mean (±SE) virus titer |
| S3.1 800 μg | 0/4 | ≤1.5 ± 0 * | 2/4 | 2.5 ± 0.47 |
| S3.1 200 μg | 0/4 | ≤1.5 ± 0 * | 4/4 | 3.4 ± 0.41 |
| S3.1 50 μg | 2/4 | 3.2 ± 1.36 | 4/4 | 4.8 ± 0.75 |
| Control 800 μg | 4/4 | 7.5 ± 0.1 | 4/4 | 6.4 ± 0.41 |

* The lower limit of detection of infectious virus in a 10% w/v suspension of lung homogenate was 1.5 log$_{10}$TCID$_{50}$/gm and in 5% w/v suspension of nasal turbinates was 1.8 log$_{10}$TCID$_{50}$/gm. These values thus indicate no detectable virus.

Mice that received S3.1 mAb were thus protected from replication of challenge virus, particularly in the lower respiratory tract. The differences in viral titers when compared to the control were statistically significantly (p<0.05) in a Student's t-test. Significant restriction of virus replication in the upper respiratory tract was noted in the mice which received the highest dose of S3.1 mAb.

Example 8

R-848

R-848 is an agonist of TLR7 and TLR8. This compound was compared with CpG 2006 in terms of efficiency of EBV-induced immortalization of human B cells. Memory B cells were isolated from healthy donors using anti-CD19 or anti-CD22 magnetic microbeads followed by negative depletion of cells carrying IgM, IgD and IgA (or IgG). 48 replicate cultures were set up in 96 well U-bottomed microplates by limiting dilution at 30, 10 and 3 B cells per well in complete medium in the presence of irradiated mononuclear cells, EBV (20% supernatant from B95-8 cells) and in the presence or absence of 2.5 µg/ml CpG 2006 or 2.5 µg/ml R-848. The frequency of cultures positive for cell growth and Ig production was measured after 14 days and the efficiency of transformation was calculated. Results were as follows:

| B cell source | EBV | +CpG 2006 | +R848 |
|---|---|---|---|
| Donor AOS CD19$^+$ IgM$^-$ IgD$^-$ IgA$^-$ | 1 in 150 | 1 in 3.5 | 1 in 2.5 |
| Donor AOS CD22$^+$ IgM$^-$ IgD$^-$ IgA$^-$ | 1 in 300 | 1 in 2 | 1 in 1.5 |
| Donor ASC CD19$^+$ IgM$^-$ IgD$^-$ IgA$^-$ | 1 in 320 | 1 in 2 | 1 in 2.4 |
| Donor ASC CD19$^+$ IgM$^-$ IgD$^-$ IgG$^-$ | 1 in 280 | 1 in 4 | 1 in 2.2 |
| Donor ETR CD22$^+$ IgM$^-$ IgD$^-$ | 1 in 230 | 1 in 1.9 | 1 in 2 |

R-848 and CpG 2006 are thus comparable in their capacity to increase the efficiency of EBV-induced immortalization. In addition, R-848 was comparable to CpG 2006 in the capacity to increase the cloning efficiency of polyclonal EBV-immortalized B cell lines. In the presence of R-848 the cloning efficiency of EBV cell lines ranged from 25 to 100% in 10 independent experiments.

Example 9

Isolation of High Affinity Antibodies Neutralizing SARS-CoV

A new series of monoclonal antibodies with SARS-CoV neutralizing capacity was produced as described above from immortalized memory B cells isolated from a convalescent patient six months after infection. Serial dilutions of supernatants from the B cell clones were tested for their antigen specificity (NP, matrix (M) or spike proteins), and their capacity to neutralize the cytopathic effect of SARS CoV (Frankfurt isolate) on Vero cells. The concentration of monoclonal IgG was measured by ELISA in the same culture supernatants. Neutralizing titers were expressed as the final concentration of IgG (ng IgG per ml) in tissue culture capable of completely neutralizing the virus (mean values of at least three tests). Results were as follows:

| B cell clone | Isotype | Specificity | Neutralizing titer |
|---|---|---|---|
| S18.1 | IgG, κ | NP | — |
| S20.1 | IgG, λ | NP | — |
| S21.1 | IgG, κ | NP | — |
| S23.4 | IgG, κ | NP | — |
| S24.1 | IgG, λ | NP | — |
| S13.1 | IgG, κ | Not determined | — |
| S5.1 | IgG, κ | M | — |
| S3.1 | IgG, κ | Spike | 300 |
| S101.1 | IgG, κ | Spike | 40 |
| S102.1 | IgG, κ | Spike | 850 |
| S103.3 | IgG, κ | Spike | 350 |
| S104.1 | IgG, κ | Spike | 150 |
| S105.2 | IgG, κ | Spike | 150 |
| S106.1 | IgG, κ | Spike | 45 |
| S107.4 | IgG, κ | Spike | 75 |
| S108.1 | IgG, κ | Spike | 40 |
| S109.2 | IgG, κ | Spike | 80 |
| S132.9 | IgG, κ | Spike | 200 |
| S128.5 | IgG, κ | Spike | 25 |
| S127.6 | IgG, κ | Spike | 40 |
| S124.4 | IgG, κ | Spike | 40 |
| S159.1 | IgG, λ | Spike | 25 |
| S160.1 | IgG, κ | Spike | 15 |

Thus the invention is routinely able to provide antibodies that can neutralize the virus at concentrations lower than $10^{-9}$ M and even down to $10^{-10}$ M (MW of human IgG is ~150 kDa, and so 150 ng/ml is ~$10^{-9}$ M).

It will be understood that the invention has been described by way of example only and modifications may be made whilst remaining within the scope and spirit of the invention. In particular, minor modifications that do not affect the immunogenicity of the modified capsular saccharide of the present invention are also encompassed.

REFERENCES

Bernasconi et al. (2003). "A role for Toll-like receptors in acquired immunity: upregulation of TLR9 by BCR triggering in naive B cells and constitutive expression in memory B cells." Blood 101:4500-04

Bernasconi et al. (2002). "Maintenance of serological memory by polyclonal activation of human memory B cells." Science 298(5601): 2199-202.

Bron et al. (1984). "Production of human monoclonal IgG antibodies against Rhesus (D) antigen." Proc Natl Acad Sci USA 81(10): 3214-7.

Casali et al. (1986). "Human monoclonals from antigen-specific selection of B lymphocytes and transformation by EBV." Science 234(4775): 476-9.

Diebold et al. (2004). Innate Antiviral Responses by Means of TLR7-Mediated Recognition of Single-Stranded RNA. Science. 2004 Feb. 19 [Epub ahead of print]

Drosten et al. (2003) "Identification of a novel coronavirus in patients with severe acute respiratory syndrome" N Engl J Med 348(20):1967-76.

Fields et al. (1996). "Virology." Lippincott-Raven, New York. Also "Fields' Virology", 4th edition (2001) editors in chief Knipe & Howley, ISBN 0-7817-1832-5.

Giachino et al. (1995) "kappa+lambda+dual receptor B cells are present in the human peripheral repertoire." J Exp Med 181, 1245-50.

Hartmann et al. (2000). "Delineation of a CpG phosphorothioate oligodeoxynucleotide for activating primate immune responses in vitro and in vivo." J Immunol 164(3): 1617-24.

Heil et al. (2004). Species-Specific Recognition of Single-Stranded RNA via Toll-like Receptor 7 and 8. Science. 2004 Feb. 19 [Epub ahead of print]

Hemmi et al. (2002). "Small anti-viral compounds activate immune cells via the TLR7MyD88-dependent signaling pathway." Nat Immunol 3(2): 196-200.

Ifversen et al. (1993). "Effect of cell-derived growth factors and cytokines on the clonal outgrowth of EBV-infected B cells and established lymphoblastoid cell lines." Hum Antibodies Hybridomas 4(3): 115-23.

Johanson et al. (1997). "Development of a humanized monoclonal antibody (MEDI-493) with potent in vitro and in vivo activity against respiratory syncythial virus." J Infect Dis 176: 1215-24.

Karber (1931). "50% end-point calculation". Arch. Exp. Pathol. Pharmak. 162, 480-483.

Kohler & Milstein (1975). "Continuous cultures of fused cells secreting antibody of predefined specificity." Nature 256(5517): 495-7.

Kozbor & Roder (1981). "Requirements for the establishment of high-titered human monoclonal antibodies against tetanus toxoid using the Epstein-Barr virus technique." J Immunol 127(4): 1275-80.

Kozbor et al., (1982). "Human anti-tetanus toxoid monoclonal antibody secreted by EBV-transformed human B cells fused with murine myeloma." Hybridoma 1(3): 323-8.

Krieg (2002). "CpG motifs in bacterial DNA and their immune effects." Annu Rev Immunol 20: 709-60.

Krieg et al. (1995). "CpG motifs in bacterial DNA trigger direct B-cell activation." Nature 374(6522)-546-9.

Ksiazek et al. (2003). "A novel coronavirus associated with severe acute respiratory syndrome" N Engl J Med 348(20): 1953-66.

Lanzavecchia (1985). "Antigen-specific interaction between T and B cells." Nature 314(6011): 537-9.

Lundgren et al. (1983). "Monoclonal anti-parasite and anti-RBC antibodies produced by stable EBV-transformed B cell lines from malaria patients." J Immunol 131(4): 2000-3.

Medzhitov & Janeway (2000). "Innate immune recognition: mechanisms and pathways." Immunol Rev 173:89-97.

Medzhitov & Janeway (2002). "Decoding the patterns of self and nonself by the innate immune system" Science 296: 298-300.

Rosen et al. "Polyclonal Ig production after Epstein-Barr virus infection of human lymphocytes in vitro." Nature 267(5607): 52-4.

Rosen et al. (1983). "Human monoclonal antibodies to a genus-specific chlamydial antigen, produced by EBV-transformed B cells." J Immunol 130(6): 2899-902.

Schneider et al. (1999) "BAFF, a novel ligand of the tumor necrosis factor family, stimulates B cell growth". J Exp Med 189(11):1747-56.

Steinitz et al. (1980). "Continuous production of monoclonal rheumatoid factor by EBV-transformed lymphocytes." Nature 287(5781): 443-5.

Steinitz et al. (1977). "EB virus-induced B lymphocyte cell lines producing specific antibody." Nature 269(5627): 420-2.

Steinitz et al. (1984). "Human anti-pneumococci antibody produced by an Epstein Barr virus (EBV)-immortalized cell line." J Immunol 132(2): 877-82.

Takeda et al. (2003). Toll-like receptors. Annu Rev Immunol 21, 335-376

Thompson et al. (1986). "The efficient production of stable, human monoclonal antibody-secreting hybridomas from EBV-transformed lymphocytes using the mouse myeloma X63-Ag8.653 as a fusion partner." J Immunol Methods 94(1-2): 7-12.

---

---

The invention claimed is:

1. A method for producing immortalized memory B lymphocytes comprising contacting memory B lymphocytes with Epstein Barr virus ("EBV") and an agonist of a Pattern Recognition Receptor that is expressed on memory B cells.

2. A method for producing a clone of an immortalized memory B lymphocyte capable of producing a monoclonal antibody with a desired antigen specificity, comprising the steps of:
   (i) producing immortalized memory B lymphocytes comprising contacting the memory B lymphocytes with EBV and an agonist of a Pattern Recognition Receptor that is expressed on memory B cells;
   (ii) screening said immortalized memory B lymphocytes for antigen specificity; and
   (iii) isolating an immortalized memory B lymphocyte clone capable of producing a monoclonal antibody having said desired antigen specificity.

3. A method for producing immortalised memory B lymphocytes, comprising:
   (i) incubating or pulsing a population of cells comprising memory B lymphocytes with EBV;
   (ii) diluting said population of cells with culture medium;
   (iii) contacting said diluted population of cells with a polyclonal B cell activator, wherein the polyclonal B cell activator is an agonist of a Pattern Recognition Receptor that is expressed on memory B cells.

4. A method for producing immortalized memory B lymphocytes, comprising:
   (i) increasing the concentration of memory B lymphocytes in a population of cells comprising memory B lymphocytes, or depleting undesired cells from the population of cells comprising memory B lymphocytes;
(ii) incubating or pulsing said population of cells with EBV;
(iii) diluting said population of cells with culture medium;
(iv) contacting said diluted population of cells with a polyclonal B cell activator, wherein the polyclonal B cell activator is an agonist of a Pattern Recognition Receptor that is expressed on memory B cells.

5. The method of any one of claim 1, 2, 3 or 4, wherein said Pattern Recognition Receptor is a Toll Like Receptor ("TLR") that is expressed on memory B cells.

6. The method of any one of claim 1, 2, 3 or 4, wherein said Pattern Recognition Receptor is Toll Like Receptor 7 (TLR7), Toll Like Receptor 9 (TLR9) and/or Toll Like Receptor 10 (TLR10).

7. The method of any one of claim 1, 2, 3 or 4, wherein said agonist of said Pattern Recognition Receptor is selected from the group consisting of: CpG oligodeoxynucleotides; R-848 and other imidazoquinoline compounds that stimulate TLRs; imiquimod; loxoribine; 7-thia-8-oxoguanosine; 7-deazaguanosine; monoclonal antibodies that mimic the effects of these activators and other synthetic compounds that trigger TLR7 and TLR8.

8. The method of any one of claim 1, 2, 3, or 4, wherein the agonist of said Pattern Recognition Receptor is CpG 2006 (SEQ ID NO: 1).

9. The method of claim 4, wherein said polyclonal B cell activator is CpG oligodeoxynucleotide, and wherein a second polyclonal B cell activator is used in combination with the CpG oligodeoxynucleotide.

10. The method of claim 3 or 4, wherein limiting dilution is used to dilute the population of cells comprising memory B lymphocytes.

11. The method of claim 3 or 4, wherein limiting dilution is used to dilute the population of cells comprising memory B lymphocytes to 30 cells, 10 cells, or 3 cells per well of a multi-well microplate.

12. The method of any one of claim 1, 2, 3 or 4, further comprising contacting the memory B lymphocytes with a stimulant of cellular growth, differentiation or survival.

13. The method of claim 12, wherein the stimulant is a cytokine.

14. The method of claim 13, wherein the cytokine is IL-2 or IL-15.

15. The method of any one of claim 1, 2, 3 or 4, wherein the memory B lymphocytes are human memory B lymphocytes.

16. The method of claim 2, wherein the cloning is carried out using limiting dilution.

17. The method of any one of claim 1, 2, 3 or 4, wherein said memory B lymphocytes are not fused with other cells.

18. The method of any one of claim 1, 2, 3 or 4, wherein a subpopulation of memory B lymphocytes with a specific antigen specificity are selected before contacting the cells with EBV or the agonist of a Pattern Recognition Receptor.

19. A method for producing a monoclonal antibody or a fragment thereof, comprising:
(i) contacting a memory B lymphocyte with EBV and an agonist of a Pattern Recognition Receptor that is expressed on memory B cells;
(ii) culturing said memory B lymphocyte; and
(iii) obtaining, and optionally, isolating said monoclonal antibody or fragment thereof.

20. A method for producing a monoclonal antibody or a fragment thereof, comprising:
(i) contacting memory B lymphocytes with EBV and an agonist of a Pattern Recognition Receptor that is expressed on memory B cells;
(ii) culturing said memory B lymphocytes;
(iii) screening said memory B lymphocytes for a desired antigen specificity;
(iv) isolating an immortalized memory B lymphocyte clone capable of producing a monoclonal antibody having said desired antigen specificity;
(v) culturing said immortalized memory B lymphocyte clone; and
(vi) obtaining, and optionally, isolating said monoclonal antibody or fragment thereof.

21. A method for producing a monoclonal antibody or a fragment thereof, comprising:
(i) producing immortalized memory B lymphocytes comprising the steps of:
(a) incubating or pulsing a population of cells comprising memory B lymphocytes with EBV;
(b) diluting said population of cells with culture medium; and
(c) contacting said diluted population of cells with a polyclonal B cell activator, wherein said polyclonal B cell activator is an agonist of a Pattern Recognition Receptor that is expressed on memory B cells;
(ii) culturing said immortalized memory B lymphocytes; and
(iii) obtaining, and optionally, isolating said monoclonal antibody or fragment thereof from said immortalized memory B lymphocytes.

22. A method for producing a monoclonal antibody or a fragment thereof, comprising:
(i) producing immortalized memory B lymphocytes comprising the steps of:
(a) increasing the concentration of memory B lymphocytes in a population of cells comprising memory B lymphocytes, or depleting undesired cells from said population of cells comprising memory B lymphocytes;
(b) incubating or pulsing said population of cells with EBV;
(c) diluting said population of cells with culture medium; and
(d) contacting said diluted population of cells with a polyclonal B cell activator, wherein said polyclonal B cell activator is an agonist of a Pattern Recognition Receptor that is expressed on memory B cells;
(ii) culturing said immortalized memory B lymphocytes; and
(iii) obtaining, and optionally, isolating said monoclonal antibody or fragment thereof from said immortalized memory B lymphocytes.

23. A method for producing a monoclonal antibody or an antigen binding fragment thereof, comprising the steps of:
(i) contacting a memory B lymphocyte with EBV and an agonist of a Pattern Recognition Receptor;
(ii) culturing said memory B lymphocyte;
(iii) obtaining and/or sequencing nucleic acid that encodes an antibody, or fragment thereof, from said memory B lymphocyte;
(iv) inserting said nucleic acid into an expression host, or using said nucleic acid sequence to prepare an expression host, in order to permit expression of said antibody, or fragment thereof, in said host; and (v) expressing said antibody, or antigen-binding fragment thereof, in said host.

24. A method for producing a monoclonal antibody or an antigen binding fragment thereof, comprising the steps of:
(i) contacting memory B lymphocytes with EBV and an agonist of a Pattern Recognition Receptor that is expressed on memory B cells;
(ii) culturing said memory B lymphocytes;
(iii) screening said memory B lymphocytes for a desired antigen specificity;
(iv) isolating an immortalized memory B lymphocyte clone capable of producing a monoclonal antibody having said desired antigen specificity;
(v) obtaining and/or sequencing nucleic acid that encodes an antibody, or fragment thereof, from said immortalized memory B lymphocyte clone;
(vi) inserting said nucleic acid into an expression host, or using said nucleic acid sequence to prepare an expression host, in order to permit expression of said antibody, or fragment thereof, in said host; and
(vii) expressing said antibody, or antigen-binding fragment thereof, in said host.

25. A method for producing a monoclonal antibody or an antigen binding fragment thereof, comprising the steps of:
(i) producing immortalized memory B lymphocytes comprising the steps of:
(a) incubating or pulsing a population of cells comprising memory B lymphocytes with EBV;
(b) diluting said population of cells with culture medium; and
(c) contacting said diluted population of cells with a polyclonal B cell activator, wherein said polyclonal B cell activator is an agonist of a Pattern Recognition Receptor that is expressed on memory B cells;
(ii) obtaining and/or sequencing nucleic acid that encodes an antibody, or fragment thereof, from said immortalized memory B lymphocytes;
(iii) inserting said nucleic acid into an expression host, or using said nucleic acid sequence to prepare an expression host, in order to permit expression of said antibody, or fragment thereof, in said host; and
(iv) expressing said antibody, or antigen-binding fragment thereof, in said host.

26. A method for producing a monoclonal antibody or a fragment thereof, comprising:
(i) producing immortalized memory B lymphocytes comprising the steps of:
(a) increasing the concentration of memory B lymphocytes in a population of cells comprising memory B lymphocytes, or depleting undesired cells from said population of cells comprising memory B lymphocytes;
(b) incubating or pulsing said population of cells with EBV;
(c) diluting said population of cells with culture medium; and
(d) contacting said diluted population of cells with a polyclonal B cell activator, wherein said polyclonal B cell activator is an agonist of a Pattern Recognition Receptor that is expressed on memory B cells;
(ii) obtaining and/or sequencing nucleic acid that encodes an antibody, or fragment thereof, from said immortalized memory B lymphocytes;
(iii) inserting said nucleic acid into an expression host, or using said nucleic acid sequence to prepare an expression host, in order to permit expression of said antibody, or fragment thereof, in said host; and
(iv) expressing said antibody, or antigen-binding fragment thereof, in said host.

27. The method of any one of claim 19, 20, 21, 22, 23, 24, 25 or 26, further comprising the step of admixing the monoclonal antibody with a pharmaceutically acceptable carrier.

28. The method of any one of claim 23, 24, 25 or 26, further comprising the step of isolating said expressed antibody.

29. The method of claim 23, 24, 25 or 26, wherein said nucleic acid or nucleic acid sequence is manipulated before said inserting step to introduce restriction sites, to change codon usage, or optimize transcription or translation regulatory sequences.

30. The method of claim 29, further comprising the step of admixing the monoclonal antibody with a pharmaceutically acceptable carrier.

* * * * *

SEQUENCE LISTING

```
<160> NUMBER OF SEQ ID NOS: 1

<210> SEQ ID NO 1
<211> LENGTH: 24
<212> TYPE: DNA
<213> ORGANISM: Artificial Sequence
<220> FEATURE:
<223> OTHER INFORMATION: Synthetic Construct

<400> SEQUENCE: 1
tcgtcgtttt gtcgttttgt cgtt                                           24
```